(12) United States Patent
Harms et al.

(10) Patent No.: US 6,814,935 B2
(45) Date of Patent: Nov. 9, 2004

(54) SAMPLE PROCESSING DEVICES AND CARRIERS

(75) Inventors: Michael R. Harms, Mendota Heights, MN (US); William Bedingham, Woodbury, MN (US); Christopher R. Kokaisel, Mendota Heights, MN (US); Barry W. Robole, Woodville, WI (US); Kenneth B. Wood, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 427 days.

(21) Appl. No.: 09/895,001

(22) Filed: Jun. 28, 2001

(65) Prior Publication Data

US 2002/0048533 A1 Apr. 25, 2002

Related U.S. Application Data

(63) Continuation-in-part of application No. 09/710,184, filed on Nov. 10, 2000, now Pat. No. 6,627,159.
(60) Provisional application No. 60/214,508, filed on Jun. 28, 2000.

(51) Int. Cl.[7] ................ B01L 3/00; B01L 3/02; G01N 21/00; G01N 31/22; G01N 15/06
(52) U.S. Cl. .......... 422/99; 422/100; 422/102; 422/68.1; 422/58; 422/60; 436/174; 436/180
(58) Field of Search ................. 436/174, 180; 422/99, 100, 68.1, 58, 60, 61, 102

(56) References Cited

U.S. PATENT DOCUMENTS

| | | |
|---|---|---|
| 4,390,499 A | 6/1983 | Curtis et al. ............ 422/72 |
| 4,673,657 A | 6/1987 | Christian |
| 4,806,316 A | 2/1989 | Johnson et al. ........ 422/100 |
| 5,049,591 A | 9/1991 | Hayashi et al. |
| 5,128,197 A | 7/1992 | Kobayashi et al. |

(List continued on next page.)

FOREIGN PATENT DOCUMENTS

| | | |
|---|---|---|
| EP | 0 169 306 | 1/1986 |
| EP | 0 402 994 A2 | 12/1990 |

(List continued on next page.)

OTHER PUBLICATIONS

Unger et al., "Monolithic Microfabricated Valves and Pumps by Multilayer Soft Lithography," SCIENCE vol. 288, Apr. 7, 2000, pp. 113–116 XP002192277.

*Handbook of Pressure Sensitive Adhesive Technology*, Donatas Satas (Ed.) 2nd Edition, p. 172, and FIG. 8–16 on p. 173, Van Nostrand Reinhold, New York, NY, 1989.

*Handbook of Pressure Sensitive Adhesive Technology*, 3rd Edition, p. 508–517.

*Test Methods for Pressure Sensitive Adhesive Tapes*, Pressure Sensitive Tape Council, (1996).

*Primary Examiner*—Jill Warden
*Assistant Examiner*—Brian R. Gordon
(74) *Attorney, Agent, or Firm*—Christopher D. Gram; Robert W. Sprague

(57) ABSTRACT

Methods and devices for thermal processing of multiple samples at the same time are disclosed. The assemblies include carriers and sample processing devices with process arrays that include conduits useful in distributing sample materials to a group pf process chambers located in fluid communication with the main conduits. The sample processing devices may include one or more of the following features in various combinations: deformable seals, process chambers connected to the main conduit by feeder conduits exiting the main conduit at offset locations, U-shaped loading chambers, and a combination of melt bonded and adhesively bonded areas. The carriers may be used to apply selective compression to the sample processing devices.

86 Claims, 19 Drawing Sheets

U.S. PATENT DOCUMENTS

| | | | |
|---|---|---|---|
| 5,135,786 A | | 8/1992 | Hayashi et al. |
| 5,139,832 A | | 8/1992 | Hayashi et al. |
| 5,145,935 A | | 9/1992 | Hayashi |
| 5,154,888 A | | 10/1992 | Zander et al. ................ 422/58 |
| 5,219,526 A | | 6/1993 | Long ........................... 422/64 |
| 5,229,297 A | * | 7/1993 | Schnipelsky et al. ......... 436/94 |
| 5,248,479 A | | 9/1993 | Parsons et al. ............... 422/58 |
| 5,254,479 A | * | 10/1993 | Chemelli .................... 436/180 |
| 5,258,163 A | | 11/1993 | Krause et al. ................ 422/58 |
| 5,278,377 A | | 1/1994 | Tsai |
| 5,288,463 A | | 2/1994 | Chemelli ..................... 422/58 |
| 5,310,523 A | | 5/1994 | Smethers et al. ............. 422/57 |
| 5,422,271 A | | 6/1995 | Chen et al. ................. 435/287 |
| 5,446,270 A | | 8/1995 | Chamberlain et al. |
| 5,461,134 A | | 10/1995 | Leir et al. |
| 5,529,708 A | | 6/1996 | Palmgren et al. |
| 5,587,128 A | | 12/1996 | Wilding et al. ............... 422/50 |
| 5,643,738 A | | 7/1997 | Zanzucchi et al. ............. 435/6 |
| 5,721,123 A | | 2/1998 | Hayes et al. |
| 5,726,026 A | | 3/1998 | Wilding et al. ............ 435/7.21 |
| 5,804,141 A | * | 9/1998 | Chianese ..................... 422/63 |
| 5,811,296 A | | 9/1998 | Chemelli et al. ........... 435/287 |
| 5,833,923 A | | 11/1998 | McClintock et al. ......... 422/52 |
| 5,863,502 A | | 1/1999 | Southgate et al. .......... 422/585 |
| 5,863,801 A | * | 1/1999 | Southgate et al. ............ 436/63 |
| 5,876,675 A | | 3/1999 | Kennedy ..................... 422/99 |
| 5,925,455 A | | 7/1999 | Bruzzone et al. |
| 6,007,914 A | | 12/1999 | Joseph et al. |
| 6,013,513 A | | 1/2000 | Reber et al. |
| 6,030,581 A | | 2/2000 | Virtanen |
| 6,063,589 A | | 5/2000 | Kellogg et al. |
| 6,143,248 A | | 11/2000 | Kellogg et al. |
| 6,184,029 B1 | | 2/2001 | Wilding et al. ............. 435/287 |
| 6,319,469 B1 | | 11/2001 | Mian et al. |
| 6,399,025 B1 | | 6/2002 | Chow ........................ 422/102 |
| 6,413,782 B1 | | 7/2002 | Parce et al. ................. 436/514 |
| 6,627,159 B1 | * | 9/2003 | Bedingham et al. ........ 422/100 |
| 6,645,758 B1 | * | 11/2003 | Schnipelsky et al. .... 435/287.2 |
| 2002/0031836 A1 | * | 3/2002 | Feldstein .................... 436/180 |
| 2003/0152994 A1 | | 8/2003 | Woudenberg et al. |
| 2003/0228701 A1 | | 12/2003 | Wong et al. |
| 2004/0018117 A1 | | 1/2004 | Desmond et al. |
| 2004/0023371 A1 | | 2/2004 | Fawcett |
| 2004/0121471 A1 | * | 6/2004 | Dufresne et al. ............. 436/45 |

FOREIGN PATENT DOCUMENTS

| | | | |
|---|---|---|---|
| EP | 0 693 560 A2 | 1/1996 | |
| WO | WO 94/26414 | 11/1994 | ............ B01L/3/00 |
| WO | WO 9429400 | 12/1994 | |
| WO | WO 95/18676 | 7/1995 | |
| WO | WO 96/15576 A1 | 5/1996 | |
| WO | WO 96/34028 | 10/1996 | |
| WO | WO 96/34029 | 10/1996 | |
| WO | WO 96/35458 | 11/1996 | |
| WO | WO 96/41864 | 12/1996 | |
| WO | WO 97/21090 | 6/1997 | |
| WO | WO 98/07019 | 2/1998 | |
| WO | WO 98/49340 | 11/1998 | |
| WO | WO 99/09394 | 2/1999 | |
| WO | WO 99/44740 | 9/1999 | ............ B01L/3/00 |
| WO | WO 99/55827 | 11/1999 | |
| WO | WO 99/58245 | 11/1999 | |
| WO | WO 99/67639 | 12/1999 | |
| WO | WO 00/05582 | 2/2000 | |
| WO | WO 00/40750 | 7/2000 | |
| WO | WO 00/50172 | 8/2000 | |
| WO | WO 00/50642 | 8/2000 | |
| WO | WO 00/68336 | 11/2000 | |
| WO | WO 00/69560 | 11/2000 | |
| WO | WO 00/78455 | 12/2000 | |
| WO | WO 00/79285 | 12/2000 | |
| WO | WO 01/07892 A1 | 2/2001 | |
| WO | WO 04/011132 A2 | 2/2004 | |
| WO | WO 04/011148 A2 | 2/2004 | |
| WO | WO 04/011149 A1 | 2/2004 | |
| WO | WO 04/011365 A2 | 2/2004 | |
| WO | WO 04/011592 A2 | 2/2004 | |

* cited by examiner

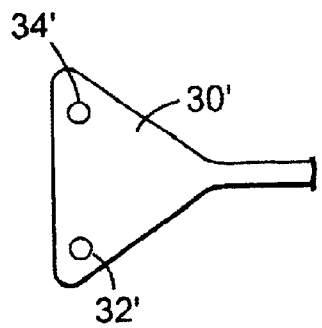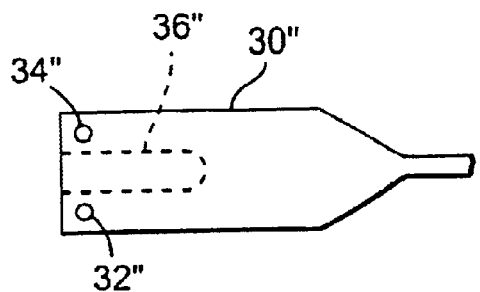
Fig. 2A  Fig. 2B
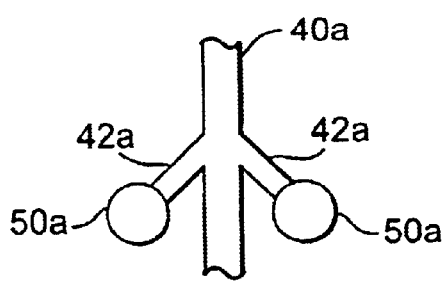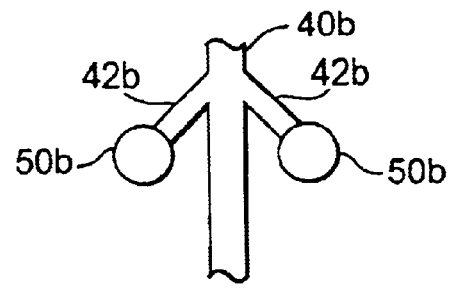
Fig. 3A  Fig. 3B
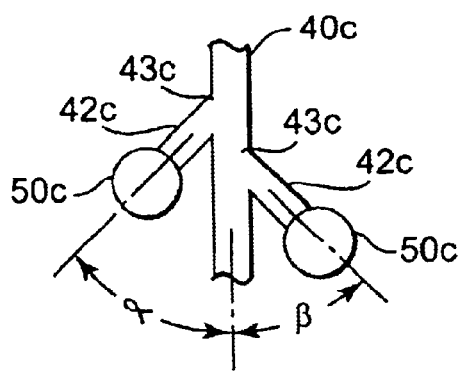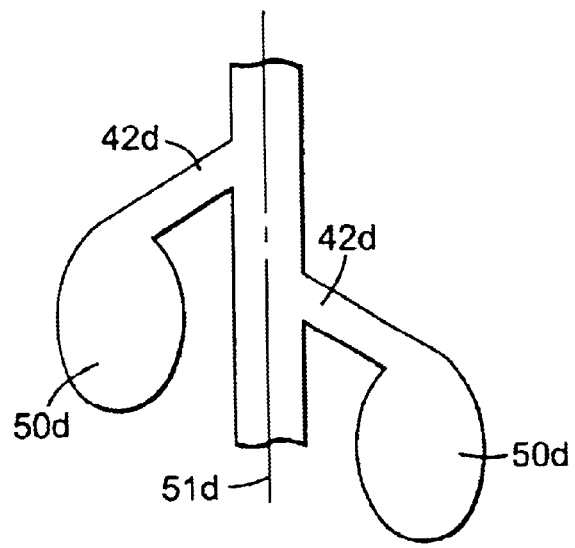
Fig. 3C  Fig. 3D

SAMPLE PROCESSING DEVICES AND CARRIERS

RELATED APPLICATIONS

This application claims the benefit of U.S. Provisional Patent Application Ser. No. 60/214,508 filed on Jun. 28, 2000 and titled THERMAL PROCESSING DEVICES AND METHODS, which is hereby incorporated by reference in its entirety.

This application is a continuation-in-part of U.S. patent application Ser. No. 09/710,184, filed Nov. 10, 2000, titled CENTRIFUGAL FILLING OF SAMPLE PROCESSING DEVICES, now U.S. Pat. No. 6,627,159, which is hereby incorporated by reference in its entirety.

GRANT INFORMATION

The present invention may have been made with support from the U.S. Government under NIST Grant No. 70NANB8H4002. The U.S. Government may have certain rights in the inventions recited herein.

FIELD OF THE INVENTION

The present invention relates to the field of sample processing devices. More particularly, the present invention relates to assemblies of sample processing devices and carriers, as well as methods of using the sample processing devices.

BACKGROUND

Many different chemical, biochemical, and other reactions are sensitive to temperature variations. The reactions may be enhanced or inhibited based on the temperatures of the materials involved. In many such reactions, a temperature variation of even 1 or 2 degrees Celsius may have a significantly adverse impact on the reaction. Although it may be possible to process samples individually and obtain accurate sample-to-sample results, individual processing can be time-consuming and expensive.

One approach to reducing the time and cost of processing multiple samples is to use a device including multiple chambers in which different portions of one sample or different samples can be processed simultaneously. However, this approach presents several temperature control related issues. When using multiple chambers, the temperature uniformity from chamber to chamber may be difficult to control. Another problem involves the speed or rate at which temperature transitions occur when thermal processing, such as when thermal cycling. Still another problem is the overall length of time required to thermal cycle a sample(s).

The multiple chamber device may include a distribution system. However, the distribution system presents the potential for cross-contamination. Sample may inadvertently flow among the chambers during processing, thereby potentially adversely impacting the reaction(s) occurring in the chambers. This may be particularly significant when multiple samples are being processed. In addition, the distribution system may present problems when smaller than usual samples are available, because the distribution system is in fluid communication with all of the process chambers. As a result, it is typically not possible to prevent delivery of sample materials to all of the process chambers to adapt to the smaller volume samples.

Thermal processing, in and of itself, presents an issue in that the materials used in the devices may need to be robust enough to withstand repeated temperature cycles during, e.g., thermal cycling processes such as PCR. The robustness of the devices may be more important when the device uses a sealed or closed system.

SUMMARY OF THE INVENTION

The present invention provides methods and devices for thermal processing of multiple samples at the same time. The sample processing devices provide process arrays that include conduits useful in distributing sample materials to a group of process chambers located in fluid communication with the main conduits. The sample processing devices may include one or more of the following features in various combinations: deformable seals, process chambers connected to the main conduit by feeder conduits exiting the main conduit at offset locations, U-shaped loading chambers, and a combination of melt bonded and adhesively bonded areas.

If present in the sample processing devices of the present invention, deformable seals may provide for closure of the main conduits to prevent leakage. Deformable seals may also provide for isolation of the process chambers located along the main conduit, such that cross-contamination (e.g., migration of reagent between process chambers after introduction of sample material) between the process chambers may be reduced or eliminated, particularly during sample processing, e.g. thermal cycling. Deformable seals may also provide the opportunity to tailor the devices for specific test protocols by closing the distribution channels leading to selected process chambers before distributing sample materials. Alternatively, some deformable seals may be closed to adjust for smaller sample material volumes reducing the number of process chambers to which the sample materials are distributed.

Sample processing devices of the present invention that include feeder conduits connecting the process chambers to the main conduits may preferably do so using feeder conduits that exit the main conduit at different locations along the main conduit, such that no main conduit/feeder conduit junctions are directly aligned across the main conduit. Such an arrangement may provide further reductions in the possibility of cross-contamination between process chambers by providing a longer path length between the process chambers.

Loading structures in the form of U-shaped loading chambers, where provided, may provide advantages in filling of the loading chambers by providing a structure from which air (or any other fluid located in the loading chamber) can escape during filling.

Sample processing devices that include both melt bonded and adhesive bonded areas may provide the advantage of capitalizing on the properties of both attachment methods in a single device. For example, it may be preferred to use melt bonding in the areas occupied by the process chambers to take advantage of the strength of the melt bonds. In the same device, it may be possible to take advantage of the sealing properties of the adhesive bonded areas.

In other aspects, the sample processing devices of the present invention may be used in connection with carriers that may, in various embodiments, provide for selective compression of sample processing devices, either compression of discrete areas proximate the process chambers or compression of the sample processing devices in the areas outside of the process chambers. In various embodiments, the carriers may preferably provide for limited contact between themselves and the sample processing devices, limited contact between themselves and any compression structure used to compress the carrier and sample processing device assembly, and limited thermal mass. The carriers may also provide openings to allow visual access to the process chambers.

It is also preferred that the sample processing devices of the invention exhibit robustness in response to the rapid thermal changes that can be induced due to the relatively high thermal conductivity and relatively low thermal mass of the devices. This robustness may be particularly valuable when the devices are used in thermal cycling methods such as, e.g., PCR. In all thermal processing methods, the preferred devices maintain process chamber integrity despite the pressure changes associated with the temperature variations and despite the differences between thermal expansion rates of the various materials used in the devices.

Yet another advantage of the present invention is that the devices may be mass manufactured in a web-based manufacturing process in which the various components may be continuously formed and/or bonded, with the individual devices being separated from the continuous web.

As used in connection with the present invention, the following terms shall have the meanings set forth below.

"Deformable seal" (and variations thereof) means a seal that is permanently deformable under mechanical pressure (with or without a tool) to occlude a conduit along which the deformable seal is located.

"Thermal processing" (and variations thereof) means controlling (e.g., maintaining, raising, or lowering) the temperature of sample materials to obtain desired reactions. As one form of thermal processing, "thermal cycling" (and variations thereof) means sequentially changing the temperature of sample materials between two or more temperature setpoints to obtain desired reactions. Thermal cycling may involve, e.g., cycling between lower and upper temperatures, cycling between lower, upper, and at least one intermediate temperature, etc.

In one aspect, the present invention provides a sample processing assembly including a sample processing device and a carrier attached to the sample processing device. The sample processing device includes a body with a first side attached to a second side and a plurality of process arrays formed between the first and second sides. Each process array of the plurality of process arrays includes a loading structure, a main conduit with a length, a plurality of process chambers distributed along the main conduit, and a deformable seal located between the loading structure and the plurality of process chambers, wherein the main conduit is in fluid communication with the loading structure and the plurality of process chambers. The carrier includes a first surface facing the sample processing device and a second surface facing away from the sample processing device; a plurality of main conduit support rails proximate the first surface of the carrier, wherein each main conduit of the plurality of process arrays is aligned with one main conduit support rail of the plurality of main conduit support rails; and a plurality of openings formed through the first and second surfaces of the carrier, wherein each opening of the plurality of openings is aligned with one process chamber of the plurality of process chambers.

In another aspect, the present invention provides a method of processing sample materials, the method including providing a sample processing assembly that includes a sample processing device attached to a carrier. The sample processing device includes a body with a first side attached to a second side and a plurality of process arrays formed between the first and second sides. Each process array of the plurality of process arrays includes a loading structure, a main conduit with a length, and a plurality of process chambers distributed along the main conduit, wherein the main conduit is in fluid communication with the loading structure and the plurality of process chambers. Each of the process arrays also includes a deformable seal located between the loading structure and the plurality of process chambers in each process array of the plurality of process arrays. The carrier includes a first surface facing the sample processing device and a second surface facing away from the sample processing device; a plurality of main conduit support rails proximate the first surface of the carrier, wherein each main conduit of the plurality of process arrays is aligned with one main conduit support rail of the plurality of main conduit support rails; and a plurality of openings formed through the first and second surfaces of the carrier, wherein each opening of the plurality of openings is aligned with one process chamber of the plurality of process chambers. The method further includes distributing sample material to at least some of the process chambers in each process array of the plurality of process arrays through the main conduit in each of the process arrays; closing the deformable seal in each process array of the plurality of process arrays, the closing including supporting the main conduit with one of the main conduit support rails while compressing the first side and the second side of the sample processing device together along the main conduit; locating the second side of the sample processing device in contact with a thermal block; and controlling the temperature of the thermal block while the sample processing device is in contact with the thermal block.

In another aspect, the present invention provides a method of processing sample materials by providing a sample processing assembly including a sample processing device attached to a carrier. The sample processing device includes a body with a first side attached to a second side and a plurality of process arrays formed between the first and second sides. Each process array of the plurality of process arrays includes a loading structure, a main conduit with a length, and a plurality of process chambers distributed along the main conduit, wherein the main conduit is in fluid communication with the loading structure and the plurality of process chambers. The carrier includes a first surface facing the sample processing device and a second surface facing away from the sample processing device; and a plurality of openings formed through the first and second surfaces of the carrier, wherein each opening of the plurality of openings is aligned with one process chamber of the plurality of process chambers. The method further includes distributing sample material to at least some of the process chambers in each process array of the plurality of process arrays through the main conduit in each of the process arrays; locating the second side of the sample processing device in contact with a thermal block; selectively compressing the first side and second side of the sample processing device together proximate each process chamber of the plurality of process chambers, the selective compression occurring between the carrier and the thermal block; and controlling the temperature of the thermal block while the sample processing device is in contact with the thermal block.

In another aspect, the present invention provides a sample processing assembly including a sample processing device attached to a carrier. The sample processing device includes a body with a first side attached to a second side and a plurality of process arrays formed between the first and second sides. Each process array of the plurality of process arrays includes a loading structure, a main conduit with a length, and a plurality of process chambers distributed along the main conduit, wherein the main conduit is in fluid communication with the loading structure and the plurality of process chambers. The carrier includes a first surface facing the sample processing device and a second surface facing away from the sample processing device; a plurality of openings formed through the first and second surfaces of the carrier, wherein each opening of the plurality of openings is aligned with one process chamber of the plurality of process chambers; and a plurality of compression structures proximate the first surface of the carrier, each compression structure of the plurality of compression structures proximate one process chamber of the plurality of process chambers.

In another aspect the present invention provides a sample processing assembly that includes a sample processing device attached to a carrier. The sample processing device includes a body with a first side attached to a second side and a plurality of process arrays formed between the first and second sides. Each process array of the plurality of process arrays includes a loading structure, a main conduit with a length, and a plurality of process chambers distributed along the main conduit, wherein the main conduit is in fluid communication with the loading structure and the plurality of process chambers. Each process array also includes a deformable seal located between the loading structure and the plurality of process chambers in each process array of the plurality of process arrays. The carrier includes a first surface facing the sample processing device and a second surface facing away from the sample processing device; a plurality of main conduit support rails proximate the first surface of the carrier, wherein each main conduit of the plurality of process arrays is aligned with one main conduit support rail of the plurality of main conduit support rails; a plurality of openings formed through the first and second surfaces of the carrier, wherein each opening of the plurality of openings is aligned with one process chamber of the plurality of process chambers; and a plurality of compression structures proximate the first surface of the carrier, each compression structure of the plurality of compression structures proximate one process chamber of the plurality of process chambers.

In another aspect, the present invention provides a method of processing sample materials, the method including providing a sample processing assembly including a sample processing device attached to a carrier. The sample processing device includes a body with a first side attached to a second side and a plurality of process arrays formed between the first and second sides. Each process array of the plurality of process arrays includes a loading structure, a main conduit with a length, and a plurality of process chambers distributed along the main conduit, wherein the main conduit is in fluid communication with the loading structure and the plurality of process chambers. Each process array also includes a deformable seal located between the loading structure and the plurality of process chambers in each process array of the plurality of process arrays. The carrier includes a first surface facing the sample processing device and a second surface facing away from the sample processing device; a plurality of main conduit support rails proximate the first surface of the carrier, wherein each main conduit of the plurality of process arrays is aligned with one main conduit support rail of the plurality of main conduit support rails; and a plurality of openings formed through the first and second surfaces of the carrier, wherein each opening of the plurality of openings is aligned with one process chamber of the plurality of process chambers. The method further includes distributing sample material to at least some of the process chambers in each process array of the plurality of process arrays through the main conduit in each of the process arrays; closing the deformable seal in each process array of the plurality of process arrays, the closing including supporting the main conduit with one of the main conduit support rails while compressing the first side and the second side of the sample processing device together along at least a portion of the length of the main conduit; locating the second side of the sample processing device in contact with a thermal block; selectively compressing the first side and second side of the sample processing device together proximate each process chamber of the plurality of process chambers, the selective compression occurring between the carrier and the thermal block; and controlling the temperature of the thermal block while the sample processing device is in contact with the thermal block.

In another aspect, the present invention provides a method of processing sample materials, the method including providing a sample processing assembly including a sample processing device attached to a carrier. The sample processing device includes a body with a first side attached to a second side and a plurality of process arrays formed between the first and second sides. Each process array of the plurality of process arrays includes a loading structure, a main conduit with a length, and a plurality of process chambers distributed along the main conduit, wherein the main conduit is in fluid communication with the loading structure and the plurality of process chambers. Each of the process arrays also includes a deformable seal located between the loading structure and the plurality of process chambers in each process array of the plurality of process arrays. The carrier includes a first surface facing the sample processing device and a second surface facing away from the sample processing device; a plurality of main conduit support rails proximate the first surface of the carrier, wherein each main conduit of the plurality of process arrays is aligned with one main conduit support rail of the plurality of main conduit support rails; and a plurality of openings formed through the first and second surfaces of the carrier, wherein each opening of the plurality of openings is aligned with one process chamber of the plurality of process chambers. The method further includes distributing sample material to at least some of the process chambers in each process array of the plurality of process arrays through the main conduit in each of the process arrays; closing the deformable seal in each process array of the plurality of process arrays, the closing including supporting the main conduit with one of the main conduit support rails while compressing the first side and the second side of the sample processing device together along at least a portion of a length of the main conduit; separating the loading structure of each process array of the plurality of process arrays from the sample processing device; locating the second side of the sample processing device in contact with a thermal block; and controlling the temperature of the thermal block while the sample processing device is in contact with the thermal block.

In another aspect, the present invention provides a method of processing sample materials, the method including providing a sample processing assembly including a sample processing device attached to a carrier. The sample processing device includes a body with a first side attached to a second side and a plurality of process arrays formed between the first and second sides. Each process array of the plurality of process arrays includes a loading chamber, a main conduit with a length, and a plurality of process chambers distributed along the main conduit, wherein the main conduit is in fluid communication with the loading chamber and the plurality of process chambers. Each of the process arrays also includes a deformable seal located between the loading chamber and the plurality of process chambers in each process array of the plurality of process arrays. The carrier includes a first surface facing the sample processing device and a second surface facing away from the sample processing device; a plurality of main conduit support rails proximate the first surface of the carrier, wherein each main conduit of the plurality of process arrays is aligned with one main conduit support rail of the plurality of main conduit support rails; and a plurality of openings formed through the first and second surfaces of the carrier, wherein each opening of the plurality of openings is aligned with one process chamber of the plurality of process chambers. The method further includes distributing sample material to at least some of the process chambers in each process array of the plurality of process arrays through the main conduit in each of the process arrays; closing the deformable seal in each process array of the plurality of process arrays, the closing including supporting the main conduit with one of the main conduit support rails while compressing the first side and the second side of the sample processing device together along at least a portion of the length of the main conduit; separating the loading chambers of each process array of the plurality of process arrays from the sample processing device; selectively compressing the first side and second side of the sample processing device together proximate each process chamber of the plurality of process chambers, the selective compression occurring between the carrier and the thermal block; locating the second side of the sample processing device in contact with a thermal block; and controlling the temperature of the thermal block while the sample processing device is in contact with the thermal block.

In another aspect, the present invention provides an apparatus for closing deformable seals in a sample processing device that includes a plurality of process arrays formed between the first and second sides, wherein each process array of the plurality of process arrays includes a loading structure, a main conduit with a length, and a plurality of process chambers distributed along the main conduit, wherein the main conduit is in fluid communication with the loading structure and the plurality of process chambers, and further wherein each of the deformable seals is located between the loading structure and the plurality of process chambers in one process array of the plurality of process arrays. The apparatus includes a base with a cavity adapted to receive the sample processing device; a bridge operatively attached to the base, wherein the bridge is capable of traversing a sample processing device received in the cavity along a first direction; and a plurality of sealing structures mounted to the bridge, each of the sealing structures adapted to deform a portion of the sample processing device to close one of the deformable seals, wherein the plurality of sealing structures are aligned along the first direction such that each main conduit is sequentially deformed by the plurality of sealing structures.

In another aspect, the present invention provides a sample processing system including a sample processing device that includes a body with a first side attached to a second side and a plurality of process arrays formed between the first and second sides. Each process array of the plurality of process arrays includes a loading structure, a main conduit with a length, and a plurality of process chambers distributed along the main conduit, wherein the main conduit is in fluid communication with the loading structure and the plurality of process chambers. The system further includes a thermal block on which the sample processing device is located; and means for simultaneously and selectively compressing the first side and second side of the sample processing device together in a discrete area proximate each process chamber of the plurality of process chambers after locating the second side of the sample processing device in contact with a thermal block.

These and other features and advantages of the present invention are described below in connection with various illustrative embodiments of the devices and methods of the present invention.

BRIEF DESCRIPTION OF THE DRAWINGS

FIGS. 2A & 2B depict alternative loading chambers for use in sample processing devices of the invention.

FIGS. 3A–3D depict alternative arrangements of process chambers, feeder conduits and a main conduit for use in connection with the present invention.

DETAILED DESCRIPTION OF ILLUSTRATIVE EMBODIMENTS OF THE INVENTION

The present invention provides a sample processing device that can be used in the processing of liquid sample materials (or sample materials entrained in a liquid) in multiple process chambers to obtain desired reactions, e.g., PCR amplification, ligase chain reaction (LCR), self-sustaining sequence replication, enzyme kinetic studies, homogeneous ligand binding assays, and other chemical, biochemical, or other reactions that may, e.g., require precise and/or rapid thermal variations. More particularly, the present invention provides sample processing devices that include one or more process arrays, each of which include a loading chamber, a plurality of process chambers and a main conduit placing the process chambers in fluid communication with the loading chamber.

Although various constructions of illustrative embodiments are described below, sample processing devices of the present invention may be manufactured according to the principles described in U.S. Provisional Patent Application Ser. No. 60/214,508 filed on Jun. 28, 2000 and titled THERMAL PROCESSING DEVICES AND METHODS; U.S. Provisional Patent Application Ser. No. 60/214,642 filed on Jun. 28, 2000 and titled SAMPLE PROCESSING DEVICES, SYSTEMS AND METHODS; U.S. Provisional Patent Application Ser. No. 60/237,072 filed on Oct. 2, 2000 and titled SAMPLE PROCESSING DEVICES, SYSTEMS AND METHODS; and U.S. patent application Ser. No. 09/710,184, filed Nov. 10, 2000, titled CENTRIFUGAL FILLING OF SAMPLE PROCESSING DEVICES.

The documents identified above all disclose a variety of different constructions of sample processing devices that could be used to manufacture sample processing devices according to the principles of the present invention. For example, although many of the sample processing devices described herein are attached using adhesives (e.g., pressure sensitive adhesives), devices of the present invention could be manufactured using heat sealing or other bonding techniques.

Figure 1:
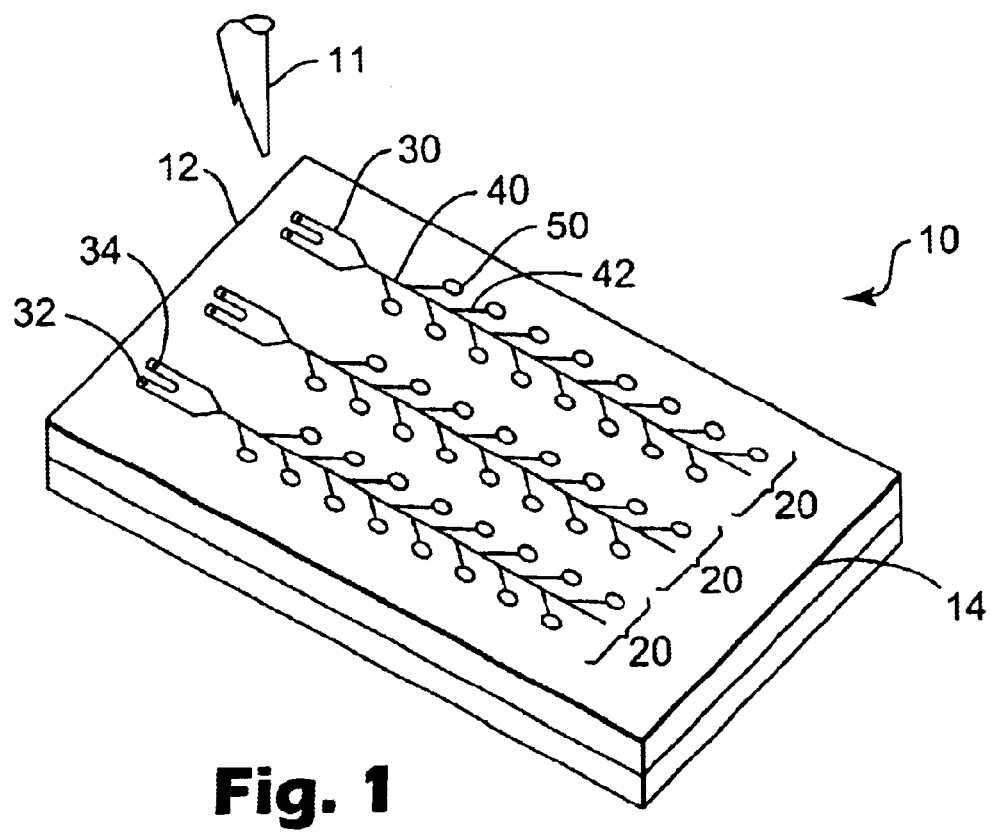
FIG. 1 is a plan view of one sample processing device of the invention.
Figure 2:
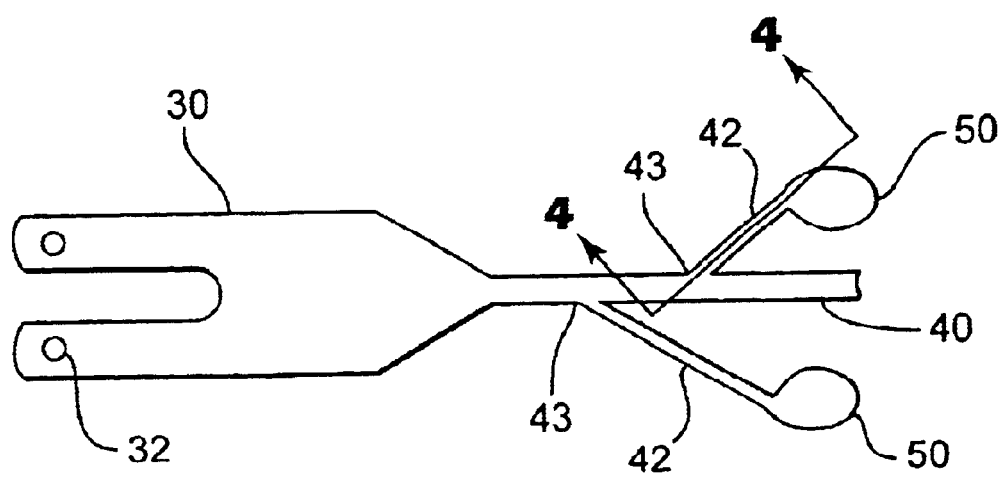
FIG. 2 is an enlarged view of a portion of one process array on the sample processing device of FIG. 1.

One illustrative sample processing device manufactured according to the principles of the present invention is illustrated in FIGS. 1 and 2, where FIG. 1 is a perspective view of one sample processing device 10 and FIG. 2 is an enlarged plan view of a portion of the sample processing device. The sample processing device 10 includes at least one, and preferably a plurality of process arrays 20. Each of the depicted process arrays 20 extends from proximate a first end 12 towards the second end 14 of the sample processing device 10.

The process arrays 20 are depicted as being substantially parallel in their arrangement on the sample processing device 10. Although this arrangement may be preferred, it will be understood that any arrangement of process arrays 20 that results in their substantial alignment between the first and second ends 12 and 14 of the device 10 may alternatively be preferred.

Alignment of the process arrays 20 may be important if the main conduits 40 of the process arrays are to be closed simultaneously as discussed in more detail below. Alignment of the process arrays 20 may also be important if sample materials are to be distributed throughout the sample processing device by rotation about an axis of rotation proximate the first end 12 of the device 10. When so rotated, any sample material located proximate the first end 12 is driven toward the second end 14 by centrifugal forces developed during the rotation.

Each of the process arrays 20 includes at least one main conduit 40, and a plurality of process chambers 50 located along each main conduit 40. The process arrays 20 also include a loading structure in fluid communication with a main conduit 40 to facilitate delivery of sample material to the process chambers 50 through the main conduit 40. It may be preferred that, as depicted in FIG. 1, each of the process arrays include only one loading structure 30 and only one main conduit 40.

The loading structure 30 may be designed to mate with an external apparatus (e.g., a pipette, hollow syringe, or other fluid delivery apparatus) to receive the sample material. The loading structure 30 itself may define a volume or it may define no specific volume, but, instead, be a location at which sample material is to be introduced. For example, the loading structure may be provided in the form of a port through which a pipette or needle is to be inserted. In one embodiment, the loading structure may be, e.g., a designated location along the main conduit that is adapted to receive a pipette, syringe needle, etc.

The loading chamber depicted in FIG. 1 is only one embodiment of a loading structure 30 in fluid communication with the main conduit 40. It may be preferred that the loading chamber volume, i.e., the volume defined by the loading chamber (if so provided), be equal to or greater than the combined volume of the main conduit 40, process chambers 50, and feeder conduits 42 (if any).

The process chambers 50 are in fluid communication with the main conduit 40 through feeder conduits 42. As a result, the loading structure 30 in each of the process arrays 20 is in fluid communication with each of the process chambers 50 located along the main conduit 40 leading to the loading structure 30. If desired, each of the process arrays 20 may also include an optional drain chamber (not shown) located at the end of the main conduit 40 opposite the loading structure 30.

If the loading structure 30 is provided in the form of a loading chamber, the loading structure 30 may include an inlet port 32 for receiving sample material into the loading structure 30. The sample material may be delivered to inlet port 32 by any suitable technique and/or equipment. A pipette 11 is depicted in FIG. 1, but is only one technique for loading sample material into the loading structures 30. The pipette 11 may be operated manually or may be part of an automated sample delivery system for loading the sample material into loading structures 30 of sample processing device 10.

Each of the loading structures 30 depicted in FIG. 1 also includes a vent port 34 with the loading structure 30. The inlet port 32 and the vent port 34 may preferably be located at the opposite ends of the legs of a U-shaped loading chamber as depicted in FIG. 1. Locating the inlet port 32 and the vent port 34 at opposite ends of the legs of a U-shaped loading chamber may assist in filling of the loading structure 30 by allowing air to escape during filling of the loading structure 30.

It should be understood, however, that the inlet ports and vent ports in loading structures 30 are optional. It may be preferred to provide loading structures that do not include preformed inlet or vent ports. In such a device, sample material may be introduced into the loading structure by piercing the chamber with, e.g., a syringe. It may be desirable to use the syringe or another device to pierce the loading structure in a one location before piercing the loading structure in a second location to fill the chamber. The first opening can then serve as a vent port to allow air (or any other gas) within the loading structure to escape during loading of the sample material.

Some potential alternative loading structures 30' and 30" are depicted in FIGS. 2A and 2B, respectively. Loading structure 30' includes an inlet port 32' and a vent port 34' in a generally wedge-shaped loading chamber. Loading structure 30" of FIG. 2B also includes an inlet port 32" and a vent port 34" in addition to a baffle 36" partially separating the loading chamber between the inlet port 32" and the vent port 34". The baffle 36" may serve the same purpose as the separate legs of the U-shaped loading chamber depicted in FIG. 1. The baffle 36" may take a variety of forms, for example, the baffle 36" may be molded into the same side of the device as the structure of the loading chamber 30", the baffle 36" may be formed by attaching the sides of the device together within the loading chamber, etc.

Each of the process arrays 20 in the sample processing devices 10 of the present invention may preferably be unvented. As used in connection with the present invention, an "unvented" process array is a process array in which the only ports leading into the volume of the process array are located in a loading chamber of the process array. In other words, to reach the process chambers within an unvented process array, sample materials must be delivered through the loading structure. Similarly, any air or other fluid located within the process array before loading with sample material must also escape from the process array through the loading structure. In contrast, a vented process array would include at least one opening outside of the loading structure. That opening would allow for the escape of any air or other fluid located within the process array before loading during distribution of the sample material within the process array.

Methods of distributing sample materials by rotating a sample processing device about an axis of rotation located proximate the loading structures are described in U.S. patent application Ser. No. 09/710,184, filed Nov. 10, 2000, titled CENTRIFUGAL FILLING OF SAMPLE PROCESSING DEVICES.

It may be preferred that, regardless of the exact method used to deliver sample materials to the process chambers through the main conduits of sample processing devices of the present invention, the result is that substantially all of the process chambers, main conduit, and feeder conduits (if any) are filled with the sample material.

The process arrays 20 depicted in FIG. 1 are arranged with the process chambers 50 located in two groups on both sides of each of the main conduits 40. The process chambers 50 are in fluid communication with the main conduit 40 through feeder conduits 42. It may be preferred that the process chambers 50 be generally circular in shape and that the feeder conduits 42 enter the process chambers 50 along a tangent. Such an orientation may facilitate filling of the process chambers 50.

The feeder conduits 42 are preferably angled off of the main conduit 40 to form a feeder conduit angle that is the included angle formed between the feeder conduit 42 and the main conduit 40. It may be preferred that the feeder conduit angle be less than 90 degrees, more preferably about 45 degrees or less. The feeder conduit angles formed by the feeder conduits 42 may be uniform or they may vary between the different process chambers 50. In another alternative, the feeder conduit angles may vary between the different sides of each of the main conduits 40. For example, the feeder conduit angles on one side of each of the main conduits 40 may be one value while the feeder conduit angles on the other side of the main conduits may be a different value.

Each of the feeder conduits 42 connects to the main conduit 40 at a feeder conduit junction 43. It may be preferred that the feeder conduit junctions 43 for the different process chambers 50 be offset along the length of the main conduit such that no two feeder conduit junctions are located directly across from each other. Such a construction may enhance isolation between the process chambers 50 during thermal processing of sample materials in the different process chambers by providing a longer diffusion path length between the process chambers 50.

FIGS. 3A–3D depict a variety of different feeder conduit and process chamber arrangements that may be used in connection with the process arrays of the present invention. The variations between arrangements may be found in the shape of the process chambers, how the feeder conduits enter the process chambers, the feeder conduit angles, and whether the feeder conduit junctions with the main conduit are aligned or offset, etc.

Turning to FIG. 3A, the process chambers 50a are connected to the main conduit 40a through feeder conduits 42a. The feeder conduits 42a are connected to the main conduit 40a at feeder conduit junctions 43a that are located directly opposite from each other across the main conduit 40a. In addition, the feeder conduits 42a enter the process chambers along a line that is not aligned with a tangent of the circular process chambers 50a. In the depicted embodiment, the centerline of each feeder conduit 42a is aligned with the center of the circular process chambers 50a, although such an arrangement is not required.

FIG. 3B depicts another arrangement of process chambers and feeder conduits that is similar in many respects to the arrangement of process chambers 50a and feeder conduits 42a depicted in FIG. 3A. One difference is that the feeder conduits 42b of FIG. 3B enter the circular process chambers 50b along a tangent to each of the process chambers 50b. One potential advantage of arranging the feeder conduits along a tangent to the process chambers 50b may include increasing the length of the feeder conduits 42b (which may improve isolation of the process chambers 50b). Another potential advantage is that entry of liquid sample materials along a tangent to the process chamber 50b may enhance mixing of the sample materials with any reagents or other constituents located within the process chamber 50b.

Another alternative arrangement of process chambers and feeder conduits is depicted in FIG. 3C where the feeder conduits 42c enter the process chambers 50c along tangents to the generally circular process chambers 50c. One difference with the arrangement depicted in FIG. 3B is that the feeder conduit junctions 43c (the points at which the feeder conduits 42c connect with the main conduit 40c) are offset along the length of the main conduit 40c. As discussed above, that offset of the feeder conduit junctions 43c may enhance process chamber isolation.

FIG. 3C also depicts another optional feature in the feeder conduit angles, i.e., that included angle formed between the feeder conduits 42c and the main conduit 40c. In FIG. 3C, the feeder conduit angle α (alpha) formed on the left side of the main conduit 40c is different than the feeder conduit angle β (beta) formed on the right side of the main conduit 40c. More specifically, the left-side feeder conduit angle α is less than the right-side feeder conduit angle β. The different feeder conduit angles may be useful to offset the feeder conduit junctions 43c when the process chambers 50c are located directly opposite each other across the main conduit 40c. Potential combinations of different feeder conduit angles may be, e.g., 25 degrees on one side and 45 degrees on the opposite side, although the particular angles chosen will vary based on a variety of factors including, but not limited to, size of the process chambers, distance between the process chambers, distance between the feeder conduit junctions with the main conduit, etc.

FIG. 3D depicts another arrangement of feeder conduits and process chambers that may be used within process arrays on sample processing devices according to the present invention. Although the process chambers illustrated in FIGS. 3A–3C are generally circular in shape, it should be understood that the a process chambers used in sample processing devices of the present invention may take any suitable shape. One example of an alternative shape is depicted in FIG. 3D in which the process chambers 50d are in the form of oval shapes that are elongated along axis 51d. The axis 51d is preferably generally aligned with the main conduit 40d. As a result, the oval-shaped process chambers 50d have their largest dimension aligned with the main conduit 40d.

FIG. 3D also depicts feeder conduits 42d that are preferably angled off of the main conduit 40d and adjoin the process chambers 50d at one end. It may be further preferred that the feeder conduits 42d meet the process chambers 50d at the end closest to the loading structures (not shown). Entry of the feeder conduits 42d into the process chambers 50d at the end may facilitate removal of air within the chambers 50d during distribution of sample material.

Figure 4:
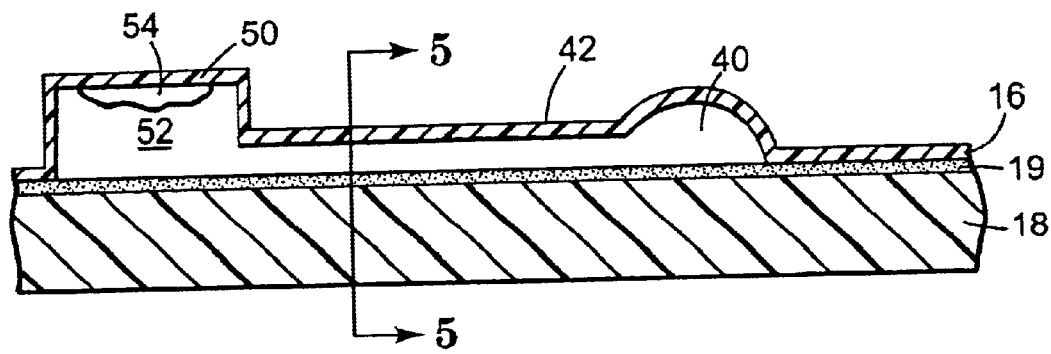
FIG. 4 is a cross-sectional view of the portion of the sample processing device of FIG. 2, taken along line 4—4 in FIG. 2.
Figure 5:
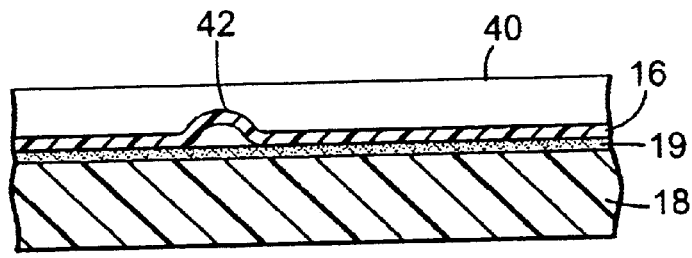
FIG. 5 is a cross-sectional view of FIG. 4, taken along FIG. 5—5 in FIG. 4.

FIGS. 4 and 5, in conjunction with FIG. 2, illustrate yet another optional feature of the sample processing devices of the present invention. FIG. 4 is a cross-sectional view of FIG. 2 taken along line 4—4 in FIG. 2 and FIG. 5 is a cross-sectional view of FIG. 2 taken along line 5—5 in FIG. 4.

It may be preferred to maintain the size of both the main conduit 40 and the feeder conduit 42 as small as possible while still allowing for adequate sample material delivery and sufficient distance between the process chambers 50 to limit diffusion. Reducing the size of the conduits 40 and 42 limits "conduit volume" within the process arrays, where conduit volume is the combined volume of the main conduit 40 and the feeder conduits 42 (where present), i.e., conduit volume does not include the volume of the process chambers 50. It may be desirable to limit the ratio of conduit volume to the total process chamber volume (i.e., the combined volume of all of the process chambers in the subject process array) to about 2:1 or less, alternatively about 1:1 or less.

One manner in which conduit volume can be limited is to reduce the cross-sectional area of the main conduit 40 and/or the feeder conduits 42 (if present in the device). It may be possible to provide feeder conduits 42 with a smaller cross-sectional area than the main conduit 40 because of the reduced length of the feeder conduits 42 as compared to the main conduit 40 (making flow restriction less of a concern in the feeder conduits). FIGS. 4 & 5 depict the smaller cross-sectional area of the feeder conduit 42 as compared to the main conduit 40. The different cross-sectional area of the conduits 40 and 42 is achieved, in the illustrated embodiment, by different heights and widths in the two conduits, although different cross-sectional areas may be achieved by varying only one of height or width in the different conduits. It may further be preferred that the height of both the main conduit 40 and feeder conduits 42 (if provided) be less than the height of the process chambers 50 as seen in FIG. 4.

It may be preferred that all of the structures forming the conduits and process chambers be provided in the first side 16 while the second side 18 is provided in the form of a generally flat sheet. In such a device, height of the conduits and process chambers can be measured above the generally flat second side 18.

FIG. 4 also depicts that process chamber 50 may include a reagent 54. It may be preferred that at least some, and preferably all, of the process chambers 50 in the devices 10 of the present invention contain at least one reagent before any sample material is distributed. The reagent 54 may be fixed within the process chamber 50 as depicted in FIG. 4. The reagent 54 is optional, i.e., sample processing devices 10 of the present invention may or may not include any reagents 54 in the process chambers 50. In another variation, some of the process chambers 50 may include a reagent 54, while others do not. In yet another variation, different process chambers 50 may contain different reagents.

The process chamber 50 also defines a volume 52. In sample processing devices of the present invention, it may be preferred that the volume 52 of the process chambers be about 5 microliters or less, alternatively about 2 microliters or less, and, in yet another alternative, about 1 microliter or less. Providing sample processing devices with micro-volume process chambers may be advantageous to reduce the amount of sample material required to load the devices, reduce thermal cycling time by reducing the thermal mass of the sample materials, etc.

Other features of the sample processing device 10 depicted in FIGS. 4 and 5 are a first side 16 and a second side 18, between which the volume 52 of process chamber 50 is formed. In addition to the process chambers 50, the main conduit 40 and the feeder conduits 42 are also formed between the first and second sides 16 and 18. Although not depicted, the loading structures, e.g., loading structures, are also formed between the first and second sides 16 and 18 of the sample processing device 10.

The major sides 16 and 18 of the device 10 may be manufactured of any suitable material or materials. Examples of suitable materials include polymeric materials (e.g., polypropylene, polyester, polycarbonate, polyethylene, etc.), metals (e.g., metal foils), etc. In one embodiment, it may be preferred to provide all of the features of the process arrays, such as the loading structures, main conduits, feeder conduits and process chambers in one side of the device, while the opposite side is provided in a generally flat sheet-like configuration. For example, it may be preferred to provide all of the features in the first side 16 in a polymeric sheet that has been molded, vacuum-formed, or otherwise processed to form the process array features. The second side 18 can then be provided as, e.g., a sheet of metal foil, polymeric material, multi-layer composite, etc. that is attached to the first side to complete formation of the process array features. It may be preferred that the materials selected for the sides of the device exhibit good water barrier properties.

By locating all of the features in one side of the sample processing device 10, the need for aligning the two sides together before attaching them may be eliminated. Furthermore, providing the sample processing device 10 with a flat side may promote intimate contact with, e.g., a thermal block (such as that used in some thermal cycling equipment). In addition, by providing all of the features in one side of the sample processing device, a reduced thermal mass may be achieved for the same process chamber volume. Further, the ability to selectively compress discrete areas about each of the process chambers may be enhanced in devices in which the structure is found on only one side thereof. Alternatively, however, it will be understood that features may be formed in both sides 16 and 18 of sample processing devices according to the present invention.

It may be preferred that at least one of the first and second sides 16 and 18 be constructed of a material or materials that substantially transmit electromagnetic energy of selected wavelengths. For example, it may be preferred that one of the first and second sides 16 and 18 be constructed of a material that allows for visual or machine monitoring of fluorescence or color changes within the process chambers 50.

It may also be preferred that at least one of the first and second sides 16 and 18 include a metallic layer, e.g., a metallic foil. If provided as a metallic foil, the side may include a passivation layer on the surfaces that face the interiors of the loading structures 30, main conduits 40, feeder conduits 42, and/or process chambers 50 to prevent contamination of the sample materials by the metal.

As an alternative to a separate passivation layer, any adhesive layer 19 used to attached the first side 16 to the second side 18 may also serve as a passivation layer to prevent contact between the sample materials and any metallic layer in the second side 18. The adhesive may also be beneficial in that it may be conformable. If so, the adhesive may provide enhanced occlusion by filling and/or sealing irregularities or surface roughness' present on either of the two sides.

In the illustrative embodiment of the sample processing device depicted in FIGS. 1 and 2, the first side 16 is preferably manufactured of a polymeric film (e.g., polypropylene) that is formed to provide structures such as the loading structures 30, main conduit 40, feeder conduits 42, and process chambers 50. The second side 18 is preferably manufactured of a metallic foil, e.g., an aluminum or other metal foil. The metallic foil is preferably deformable as discussed in more detail below.

The first and second sides 16 and 18 may be attached to each other by any suitable technique or techniques, e.g., melt bonding, adhesives, combinations of melt bonding and adhesives, etc. If melt bonded, it may be preferred that both sides 16 and 18 include, e.g., polypropylene or some other melt bondable material, to facilitate melt bonding. It may, however, be preferred that the first and second sides 16 and 18 be attached using adhesive. As depicted in FIGS. 4 and 5, the adhesive may preferably be provided in the form of a layer of adhesive 19. It may be preferred that the adhesive layer 19 be provided as a continuous, unbroken layer over the surface of at least one of the first and second sides 16 and 18. It may, for example, be preferred that the adhesive layer 19 be provided on the second side 18 and, more particularly, it may be preferred that the adhesive layer 19 cover substantially all of the surface of the second side 18 facing the first side 16.

A variety of adhesives may be used, although any adhesive selected should be capable of withstanding the forces generated during processing of any sample materials located in the process chambers 50, e.g., forces developed during distribution of the sample materials, forces developed during thermal processing of the sample materials, etc. Those forces may be large where e.g., the processing involves thermal cycling as in, e.g., polymerase chain reaction and similar processes. It may also be preferred that any adhesives used in connection with the sample processing devices exhibit low fluorescence, be compatible be the processes and materials to be used in connection with sample processing devices, e.g. PCR, etc.

It may be preferred to use adhesives that exhibit pressure sensitive properties. Such adhesives may be more amenable to high volume production of sample processing devices since they typically do not involve the high temperature bonding processes used in melt bonding, nor do they present the handling problems inherent in use of liquid adhesives, solvent bonding, ultrasonic bonding, and the like.

One well known technique for identifying pressure sensitive adhesives is the Dahlquist criterion. This criterion defines a pressure sensitive adhesive as an adhesive having a 1 second creep compliance of greater than $1\times10^{-6}$ cm$^2$/dyne as described in *Handbook of Pressure Sensitive Adhesive Technology*, Donatas Satas (Ed.), $2^{nd}$ Edition, p. 172, Van Nostrand Reinhold, New York, N.Y., 1989. Alternatively, since modulus is, to a first approximation, the inverse of creep compliance, pressure sensitive adhesives may be defined as adhesives having a Young's modulus of less than $1\times10^6$ dynes/cm$^2$. Another well known means of identifying a pressure sensitive adhesive is that it is aggressively and permanently tacky at room temperature and firmly adheres to a variety of dissimilar surfaces upon mere contact without the need of more than finger or hand pressure, and which may be removed from smooth surfaces without leaving a residue as described in *Test Methods for Pressure Sensitive Adhesive Tapes*, Pressure Sensitive Tape Council, (1996). Another suitable definition of a suitable pressure sensitive adhesive is that it preferably has a room temperature storage modulus within the area defined by the following points as plotted on a graph of modulus versus frequency at 25° C.: a range of moduli from approximately $2\times10^5$ to $4\times10^5$ dynes/cm$^2$ at a frequency of approximately 0.1 radian/second (0.017 Hz), and a range of moduli from approximately $2\times10^6$ to $8\times10^6$ dynes/cm$^2$ at a frequency of approximately 100 radians/second (17 Hz) (for example see FIGS. 8–16 on p. 173 of *Handbook of Pressure Sensitive Adhesive Technology*, Donatas Satas (Ed.), $2^{nd}$ Edition, Van Nostrand Rheinhold, New York, 1989). Any of these methods of identifying a pressure sensitive adhesive may be used to identify potentially suitable pressure sensitive adhesives for use in the methods of the present invention.

It may be preferred that the pressure sensitive adhesives used in connection with the sample processing devices of the present invention include materials which ensure that the properties of the adhesive are not adversely affected by water. For example, the pressure sensitive adhesive will preferably not lose adhesion, lose cohesive strength, soften, swell, or opacify in response to exposure to water during sample loading and processing. Also, the pressure sensitive adhesive should not contain any components which may be extracted into water during sample processing, thus possibly compromising the device performance.

In view of these considerations, it may be preferred that the pressure sensitive adhesive be composed of hydrophobic materials. As such, it may be preferred that the pressure sensitive adhesive be composed of silicone materials. That is, the pressure sensitive adhesive may be selected from the class of silicone pressure sensitive adhesive materials, based on the combination of silicone polymers and tackifying resins, as described in, for example, "Silicone Pressure Sensitive Adhesives", *Handbook of Pressure Sensitive Adhesive Technology*, 3$^{rd}$ Edition, pp. 508–517. Silicone pressure sensitive adhesives are known for their hydrophobicity, their ability to withstand high temperatures, and their ability to bond to a variety of dissimilar surfaces.

The composition of the pressure sensitive adhesives is preferably chosen to meet the stringent requirements of the present invention. Some suitable compositions may be described in International Publication WO 00/68336 titled SILICONE ADHESIVES, ARTICLES, AND METHODS (Ko et al.).

Other suitable compositions may be based on the family of silicone-polyurea based pressure sensitive adhesives. Such compositions are described in U.S. Pat. No. 5,461,134 (Leir et al.); U.S. Pat. No. 6,007,914 (Joseph et al.); International Publication No. WO 96/35458 (and its related U.S. patent application Ser. Nos. 08/427,788 (filed Apr. 25, 1995); 08/428,934 (filed Apr. 25, 1995); 08/588,157 (filed Jan. 17, 1996); and 08/588,159 (filed Jan. 17, 1996); International Publication No. WO 96/34028 (and its related U.S. patent application Ser. Nos. 08/428,299 (filed Apr. 25, 1995); 08/428,936 (filed Apr. 25, 1995); 08/569,909 (filed Dec. 8, 1995); and 08/569,877 (filed Dec. 8, 1995)); and International Publication No. WO 96/34029 (and its related U.S. patent application Ser. Nos. 08/428,735 (filed Apr. 25, 1995) and 08/591,205 (filed Jan. 17, 1996)).

Such pressure sensitive adhesives are based on the combination of silicone-polyurea polymers and tackifying agents. Tackifying agents can be chosen from within the categories of functional (reactive) and nonfunctional tackifiers as desired. The level of tackifying agent or agents can be varied as desired so as to impart the desired tackiness to the adhesive composition. For example, it may be preferred that the pressure sensitive adhesive composition be a tackified polydiorganosiloxane oligurea segmented copolymer including (a) soft polydiorganosiloxane units, hard polyisocyanate residue units, wherein the polyisocyanate residue is the polyisocyanate minus the —NCO groups, optionally, soft and/or hard organic polyamine units, wherein the residues of isocyanate units and amine units are connected by urea linkages; and (b) one or more tackifying agents (e.g., silicate resins, etc.).

Furthermore, the pressure sensitive layer of the sample processing devices of the present invention can be a single pressure sensitive adhesive or a combination or blend of two or more pressure sensitive adhesives. The pressure sensitive layers may result from solvent coating, screen printing, roller printing, melt extrusion coating, melt spraying, stripe coating, or laminating processes, for example. An adhesive layer can have a wide variety of thicknesses as long as it meets exhibits the above characteristics and properties. In order to achieve maximum bond fidelity and, if desired, to serve as a passivation layer, the adhesive layer should be continuous and free from pinholes or porosity.

Even though the sample processing devices may be manufactured with a pressure sensitive adhesive to connect the various components, e.g., sides, together, it may be preferable to increase adhesion between the components by laminating them together under elevated heat and/or pressure to ensure firm attachment of the components and sealing of the process arrays.

Another potential feature of the sample processing devices of the invention is a deformable seal that may be used to close the main conduit, isolate the process chambers 50, or accomplish both closure of the main conduit and isolation of the process chambers. As used in connection with the present invention, the deformable seals may be provided in a variety of locations and/or structures incorporated into the sample processing devices. Essentially, however, the deformable seal in a process array will be located somewhere in the fluid path between the loading chamber and the plurality of process chambers.

Figure 7:
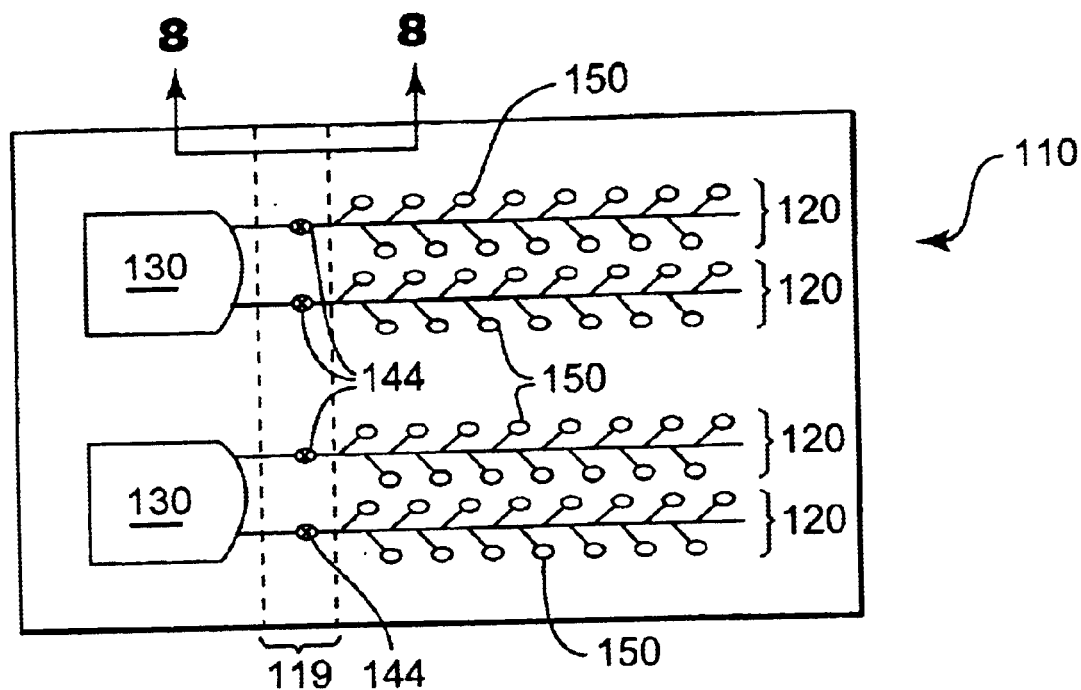
FIG. 7 depicts an alternative sample processing device of the present invention.

With respect to FIG. 1, for example, the deformable seal may be located in the main conduit 40 between the loading structure 30 and the plurality of process chambers 50 of each process array 20. In this configuration the deformable seal may extend for the substantially the entire length of the main conduit 40 or it may be limited to selected areas. For example, the deformable seal may extend along the main conduit 40 only in the areas occupied by the feeder conduits 42 leading to the process chambers 50. In another example, the deformable seal may be a composite structure of discrete sealing points located along the main conduit 40 or within each of the feeder conduits 42. Referring to FIG. 7 (described below), in another configuration, the deformable seal may be limited to the area 119 between the loading structures 130 and the plurality of process chambers 150 in each of the process arrays 120.

Closure of the deformable seals may involve plastic deformation of portions of one or both sides 16 and 18 to occlude the main conduits 40 and/or feeder conduits 42. If, for example, a pressure sensitive adhesive 19 is used to attach the first and second sides 16 and 18 of the sample processing device together, that same pressure sensitive adhesive may help to maintain occlusion of the main conduits 40 and/or feeder conduits 42 by adhering the deformed first and second sides 16 and 18 together. In addition, any conformability in the adhesive 19 may allow it to conform and/or deform to more completely fill and occlude the main conduits 40 and/or feeder conduits 42.

It should be understood, however, that complete sealing or occlusion of the deformed portions of the sample processing device 10 may not be required. For example, it may only be required that the deformation restrict flow, migration or diffusion through a conduit or other fluid pathway sufficiently to provide the desired isolation. As used in connection with the present invention, "occlusion" will include both partial occlusion and complete occlusion (unless otherwise explicitly specified). Furthermore, occlusion of the main conduit may be continuously over substantially all of the length of the main conduit or it may be accomplished over discrete portions or locations along the length of the main conduit. Also, closure of the deformable seal may be accomplished by occlusion of the feeder conduits alone and/or by occlusion of the feeder conduit/main conduit junctions (in place of, or in addition to, occlusion of a portion or all of the length of the main conduit).

In some embodiments in which the deformable seal is provided in the form of an occludable main conduit, it may be advantageous to occlude the main conduit over substantially all of its length and, in so doing, urge any sample materials within the main conduit back towards the loading chamber (e.g., as described below in connection with FIGS. 21–25). It may be preferred that the sample materials urged back towards the loading chamber are driven back into the loading chamber. As a result, the loading chambers in process arrays of the present invention may also serve as waste or purge chambers for sample materials urged out of the main conduits and/or feeder conduits during closure of the deformable seals.

Figure 6:
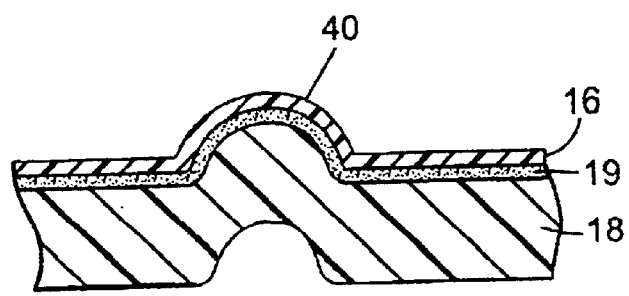
FIG. 6 is a cross-sectional view of the main conduit of FIG. 4, taken after deformation of the main conduit to isolate the process chambers.

Referring now to FIGS. 4–6, one embodiment of a deformable seal for isolating the process chambers 50 is depicted. The deformable seal is provided in the form of a deformable second side 18 that can be deformed such that it extends into the main conduit 40 as depicted in FIG. 6.

The use of adhesive to attach the first side 16 to the second side 18 may enhance closure or occlusion of the deformable seal by adhering the two sides together within the main conduit 40. It may be preferred that the adhesive 19 be a pressure sensitive adhesive in such an embodiment, although a hot melt adhesive may alternatively be used if deformation of the main conduit 40 is accompanied by the application of thermal energy sufficient to activate the hot melt adhesive.

In one method in which the process arrays 20 are closed after distribution of sample materials into process chambers 50, it may be necessary to close the deformable seal along only a portion of the main conduit 40 or, alternatively, the entire length of the distribution channel 40. Where only a portion of the main conduit 40 is deformed, it may be preferred to deform that portion of the main conduit 40 located between the loading chamber 30 and the process chambers 50.

Sealing all of the main conduit 40 by forcing the sides 16 and 18 together along the length of the conduit 40 may provide advantages such as driving any fluid located in the main conduit 40 back into the loading structure 30. One potential advantage, however, of sealing only a portion of the length of the main conduit 40 is that either none or only a small amount of any fluid material located in the main conduit 40 would be returned to the loading structure 30.

Figure 8:
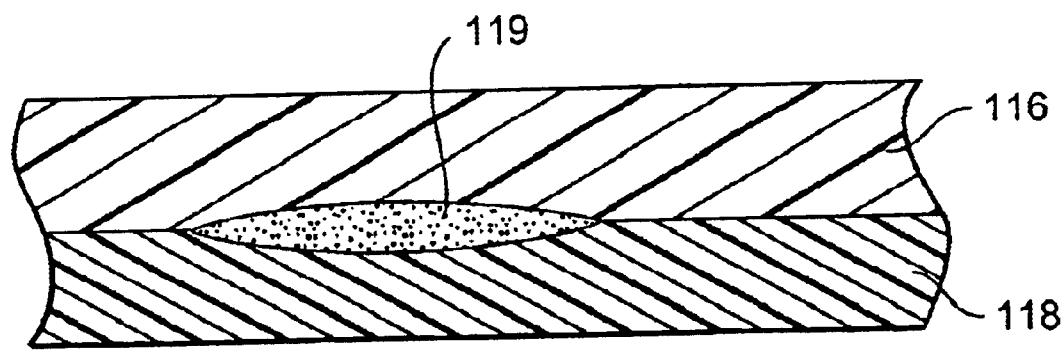
FIG. 8 is an enlarged partial cross-sectional view of the sample processing device of FIG. 7, taken along line 8—8 in FIG. 7.

FIGS. 7 & 8 depict another sample processing device 110 according to the present invention that includes a first side 116 attached to a second side 118, with a set of process arrays 120 formed between the two sides 116 and 118. One difference between the sample processing device 110 depicted in FIGS. 7 & 8 and the sample processing device of FIGS. 1 & 2 is that the sides 116 and 118 of the sample processing device 110 are attached together by the combination of a melt bond and an adhesive.

As used herein, a "melt bond" is a bond formed by the melting and/or mixing of materials such as that occurring during, e.g., heat sealing, thermal welding, ultrasonic welding, chemical welding, solvent bonding, etc. In such a device, the materials facing each other in sides 116 and 118 must be compatible with melt bonding so that a seal of sufficient integrity can be formed to withstand the forces experienced during processing of sample materials in the process chambers.

The adhesive 119 is provided only within a selected area of the sample processing device and may be provided for the dual purpose of attaching portions of the two sides 116 and 118 together and assisting with sealing or occlusion of the main conduit 140 by adhering the sides 116 and 118 together as discussed above.

It may be preferred that the selected area of pressure sensitive adhesive 119 be located between the loading chambers 130 and the process chambers 150 as seen in FIGS. 7 & 8. Although the pressure sensitive adhesive 119 is depicted as being limited to an area that does not include the loading chambers 130, it should be understood that the pressure sensitive adhesive 119 may be used to attach the two sides 116 and 118 together within the area occupied by the loading chambers 130 in addition to the area between the loading structures 130 and the process chambers 150.

By locating the pressure sensitive adhesive 119 in the area between the loading structures 130 and the process chambers 150, the main conduits 140 are directed through the pressure sensitive adhesive layer 119 such that closure or occlusion of the deformable seals can be assisted by the adhesive located between the two sides 116 and 118. Another potential advantage of attaching the two sides 116 and 118 together with a melt bond in the area occupied by the process chambers 150 is that the bond strength of the melt bond may be better suited to withstand the forces developed during thermal processing of sample materials in the process chambers 150.

FIG. 7 also depicts another arrangement of process arrays 120 that may be used in connection with sample processing devices of the present invention. Each of the process arrays 120 includes a loading structure 130. The loading structures 130 are in fluid communication with a plurality of process chambers 150 through main conduits 140.

One feature illustrated in connection with FIG. 7 is the addition of valves 144 along the main conduits 140. By selectively opening or closing the valves 144 along the main conduit 140 (which may be either closed or open when manufactured) the delivery of sample material to each set of process chambers 150 may be enabled or prevented. For example, if one of the valves 144 is open while the other valve 144 is closed, delivery of sample material will be effected only to one set of process chambers 150 (through the open valve 144).

It may be possible to achieve the same result, i.e., enabling or preventing delivery of sample material to a subset of process chambers 150, by sealing the main conduit 140 at an appropriate location after the bifurcation point. The use of valves 144 may, however, provided the ability for automated control or customization of the sample processing device including process arrays 120. The valves 144 may take any suitable form, some examples of which are described in the patent applications identified above.

By using customizable process arrays 120, it may be possible to provide sample processing devices that are tailored at the point of use for particular testing needs. Other advantages may be found in the ability to reduce the volume of sample material needed by reducing the number of process chambers 150 to which that sample material may be delivered. Alternatively, where a higher level of confidence is required, the valves 144 may be opened to increase the number of process chambers 150 to which sample material is delivered, thereby increasing the number of tests performed.

Figure 9:
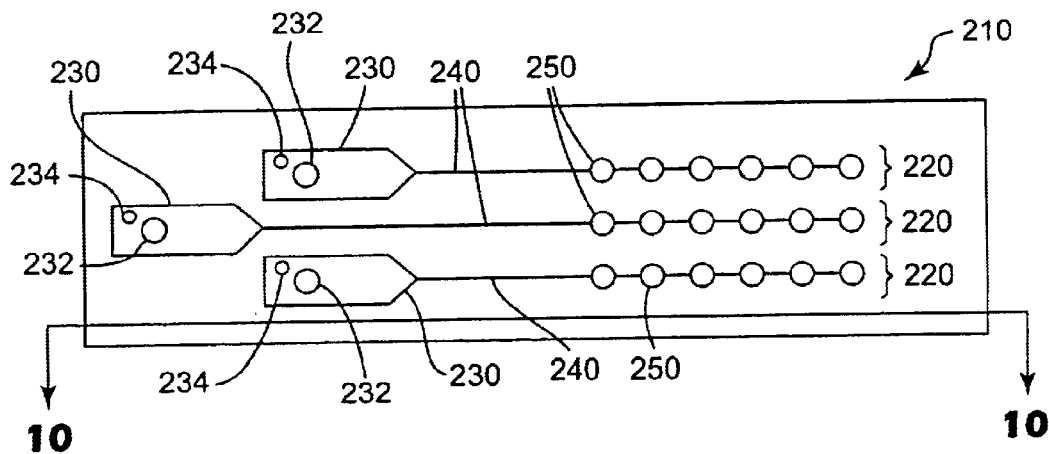
FIG. 9 depicts an alternative sample processing device of the present invention.
Figure 10:
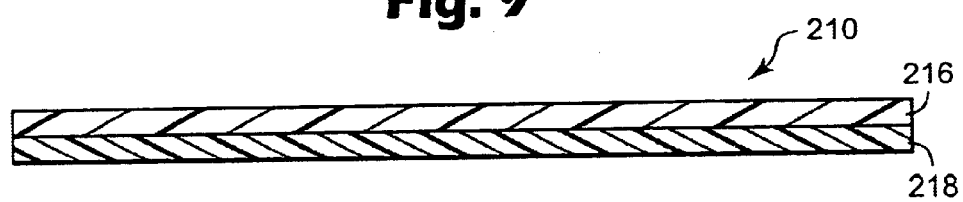
FIG. 10 is a cross-sectional view of the sample processing device of FIG. 9, taken along line 10—10 in FIG. 9.

FIGS. 9 & 10 depict another sample processing device 210 according to the present invention that includes a first side 216 attached to a second side 218, with a set of process arrays 220 formed between the two sides 216 and 218. One difference between the sample processing device 110 depicted in FIGS. 7 & 8 and the sample processing device 210 of FIGS. 9 & 10 is that the sides 216 and 218 of the sample processing device 210 are attached together by a melt bond.

FIG. 9 also depicts another arrangement for process arrays 220 useful in sample processing devices of the invention. Among the features depicted in connection with process arrays 220 are the staggered relationship between loading structures 230. Such a staggered relationship may allow for a higher density of process chambers 250 on the sample processing device.

Each of the loading structures 230 also includes a loading port 232 and a vent port 234 which may facilitate rapid filling of the loading structures 230 by providing a pathway separate from the loading port 232 for air to escape during filling of the loading structure 230.

Another feature depicted in FIG. 9 is the serial relationship between the process chambers 250 located along each of the main conduits 240. Each pair of successive process chambers 250 is in fluid communication with each other along main conduit 240. As a result, if any reagents or other materials are to be located within process chambers 250 before distribution of the sample material, then some mechanism or technique for preventing removal of those materials during distribution of the sample material must be provided. For example, the reagents may be contained in a wax or other substance within each of the process chambers 250.

Furthermore, it may be preferred that the height of the main conduits 240 between the process chambers 250 be less than the height of the process chambers 250. Such a design may improve the ability to rapidly and accurately occlude the main conduits by deforming a deformable seal structure located within the main conduits 240.

Figure 11:
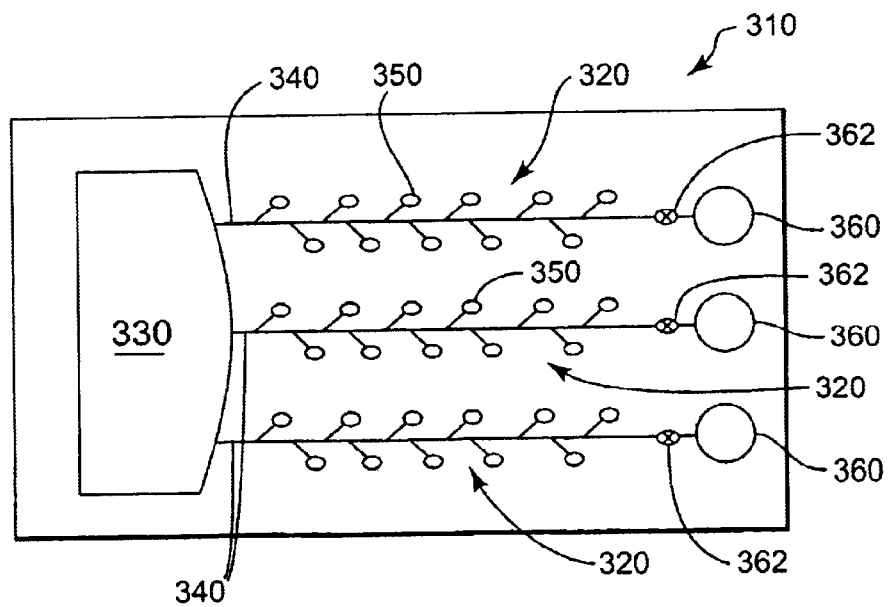
FIG. 11 depicts an alternative sample processing device of the present invention.

FIG. 11 depicts yet another arrangement of process arrays 320 on a sample processing device 310 in which the process arrays 320 share a common loading structure 330 from which a set of main conduits 340 extend. Each of the main conduits 340 connects a set of process chambers 350 to the common loading structure 330.

Another feature in the process arrays 320 of sample processing device 310 are drain chambers 360 connected to the end of the main conduits 340 that is opposite the loading structure 330. The drain chambers 360 may be separated from the main conduit by a drain valve 362 that may preferably be closed until the process chambers 350 are filled with sample material. After filling of the process chambers 350, the drain valve 362 can be opened to allow sample material remaining in the main conduits 340 and loading structure 330 to proceed into the drain chamber 360. The drain chambers 360 may allow for improved sealing or occlusion of the main conduits 340 by providing for the removal of sample materials from the main conduits 340 before sealing as discussed above.

Figure 12:
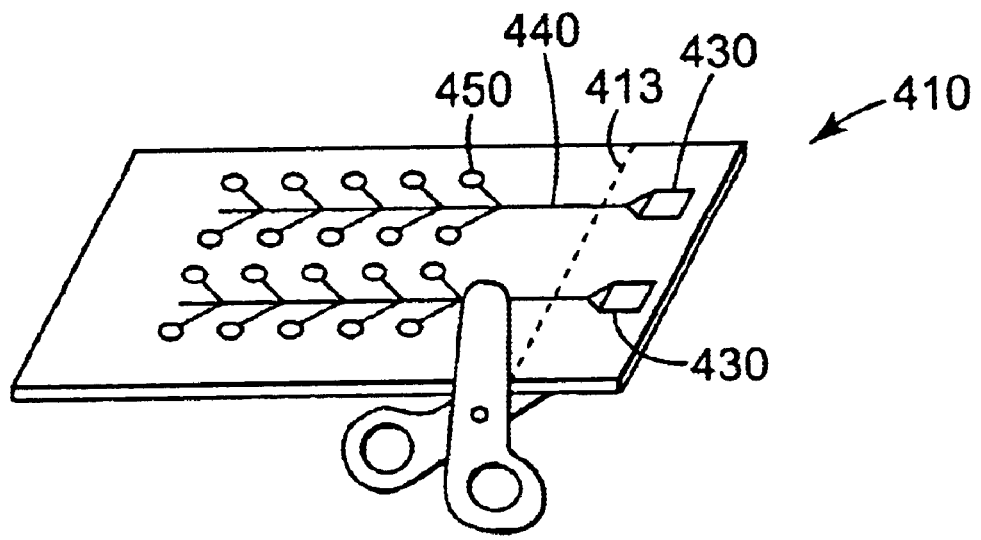
FIG. 12 is a perspective view of a sample processing device in which the loading chambers are being separated from the remainder of the sample processing device.

Referring now to FIG. 12, another optional feature of the present invention is separation of the loading structures 430 from the remainder of another embodiment of a sample processing device 410 according to the present invention. Separation of the loading portion of the sample processing device 410 from the portion containing the process chambers 450 may provide advantages such as, for example, reducing the size of the sample processing device 410, reducing the thermal mass of the sample processing device 410, removing any sample materials that may remain within the loading structures 430 after distribution to process chambers 450, etc.

Separation of the loading structures 430 from the sample processing device 410 may involve, for example, cutting the sample processing device 410 along the separation line 413 as depicted in FIG. 12. Where the loading structures 430 are to be physically separated from the remainder of the sample processing device 410, it is typically preferable that the main conduits 440 be sealed across at least the separation line 413 to prevent leakage of the sample materials during and after the separation process.

Figure 13:
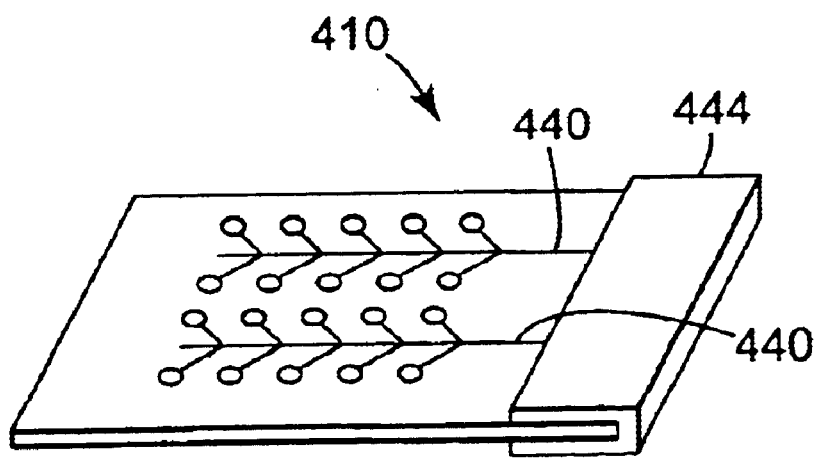
FIG. 13 is a perspective view of the sample processing device of FIG. 12 after sealing.

The use of an adhesive within the main conduits 440 (see, e.g., FIGS. 2 and 3) may be particularly helpful to ensure adequate sealing of the main conduits 440 as discussed above. If additional sealing is required, it may also be helpful to cover the ends of the main conduits with a seal 444 as illustrated in FIG. 13. The seal 444 may be provided, e.g., in the form of an adhesive coated foil or other material. Alternatively or in addition to the use of an adhesive to secure the seal 444, it may be desirable to, e.g., heat seal the seal 444 in place on the sample processing device 410.

Figure 14:
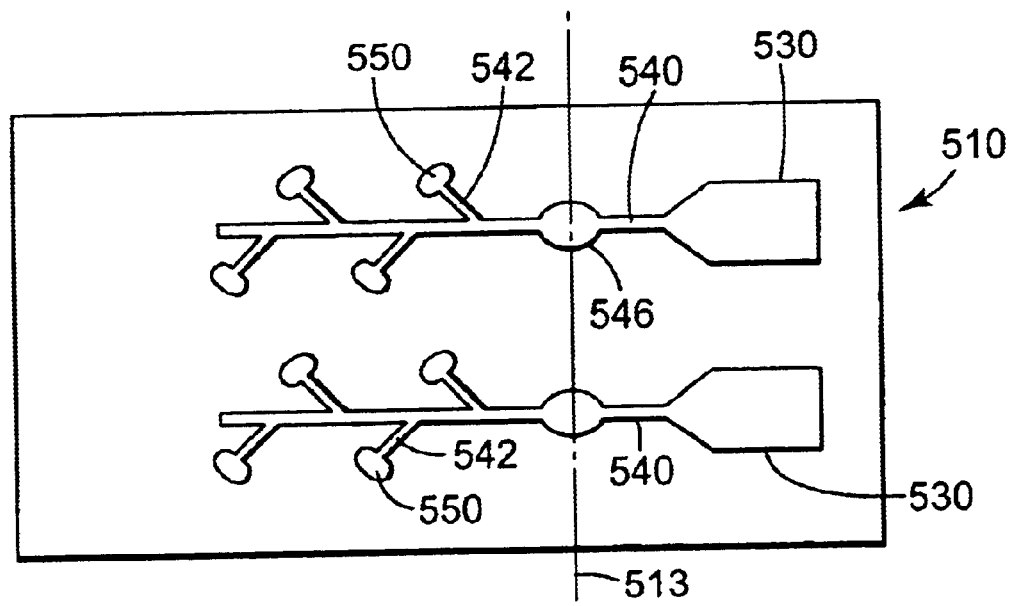
FIG. 14 is a plan view of another sample processing device.
Figure 15:
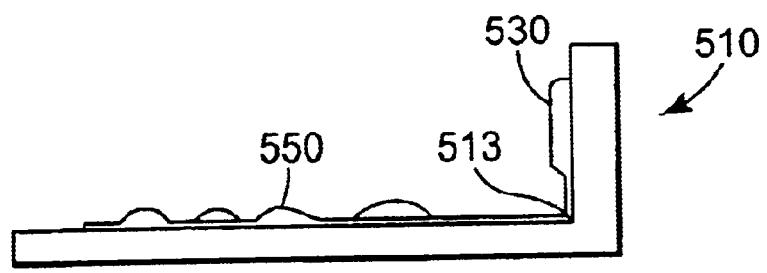
FIG. 15 is a side view of the sample processing device of FIG. 14 after folding the device along a line separating the loading chambers from the process chambers.

Referring now to FIGS. 14 and 15, one alternative to physical separation of the loading structures 530 from the remainder of the sample processing device 510 may include folding the sample processing device 510 along, e.g., separation line 513. That folding process may also close the main conduit 540 across the separation line 513 by crimping the main conduits 540, such that a desired level isolation may be achieved between the process chambers 550 without further deformation of any of the main conduits 540 or the feeder conduits 542.

It may be desirable to provide crimping areas 546 located at the intersections of the main conduits 540 with the folding line 513 that are wider and shallower than the surrounding portions of conduits 540 to facilitate crimping of the conduits 540 during folding. The wider, shallower crimping areas 546 do, however, preferably provide a cross-sectional area for fluid flow that is similar to the cross-sectional fluid flow area of the surrounding portions of the main conduits 540.

Sample processing devices may be processed alone, e.g., as depicted in FIG. 1. It may, however, be preferred to provide the sample processing device 610 mounted on a carrier 680. Such an assembly is depicted in an exploded perspective view of sample processing device 610 and carrier 680 in FIG. 16.

By providing a carrier that is separate from the sample processing device, the thermal mass of the sample processing device can be minimally affected as compared to manufacturing the entire sample processing device with a thickness suitable for handling with automated equipment (e.g., robotic arms, etc.) processing in conventional equipment. Another potential advantage of a carrier is that the sample processing devices may exhibit a tendency to curl or otherwise deviate from a planar configuration. Attaching the sample processing device to a carrier can retain the sample processing device in a planar configuration for processing.

Carriers used in connection with the sample processing devices of the invention preferably also have some preferred physical properties. For example, it may be preferred that the carriers provide limited areas of contact with the sample processing devices to which they are mounted to reduce thermal transmission between the sample processing device and the carrier. It may further be preferred that the surface of the carrier facing away from the sample processing device also provide limited areas of contact with, e.g., a platen or other structure used to force the sample processing device against a thermal block to reduce thermal transmission between the carrier and the platen or other structure. It may further be preferred that the carriers themselves have a relatively low thermal mass to avoid influencing temperature changes in the sample processing devices.

Another potentially desirable physical property of carriers manufactured according to the present invention is that they exhibit some compliance such that the carrier (and attached sample processing device) can conform to the surfaces between which the assembly is compressed, e.g., a thermal block and platen. Carriers themselves may not be perfectly planar due to, e.g., variations in manufacturing tolerances, etc. Further, the assemblies may have different thicknesses due to thickness variations in the carrier and/or the sample processing device.

If the sample processing device 610 is to be loaded using centrifugal forces developed during rotation of the sample processing devices the centrifugal forces may challenge the sealing of the process chambers and other fluid pathways in each of the process arrays. The challenges may be especially acute when the sample processing device is constructed using an adhesive to attach to layers together. A properly designed carrier may assist in maintaining the integrity of the sample processing device by providing the opportunity to apply pressure to the card during loading and/or thermal cycling.

The carrier 680 may be attached to the sample processing device 610 in a manner that allows for the carrier 680 to be reused with many different sample processing devices 610. Alternatively, each carrier 680 may be permanently attached to a single sample processing device 610 such that, after use, both the sample processing device 610 and the carrier 680 are discarded together.

In the depicted embodiment, the sample processing device 610 includes molded posts 611 for aligning the sample processing device 610 to the carrier. It may be preferred that at least one of the molded posts be located proximate a center of the sample processing device 610. Although it may be possible to provide only one molded post 611 for attaching the sample processing device 610 to the carrier 680, it may be preferred that at least two posts 611 be provided. The centrally-located post 611 may assist in centering the sample processing device 610 on the carrier 680, while the second post 611 may prevent rotation of the sample processing device 610 relative to the carrier 680. Further, although only two posts 611 are depicted, it will be understood that three or more posts or other sites of attachment between the sample processing devices 610 and the carriers 680 may be provided if desired. Further, the posts 611 may be melt bonded to the sample processing device 610 to also accomplish attachment of the two components in addition to alignment.

Posts or other alignment features may also be provided on the, e.g., the carrier 680 to generally align the sample processing device 610 on the carrier 680 before the final alignment and attachment using molded posts 611 on the sample processing device 610. The posts or other alignment features may also assist in aligning the assembly including the sample processing device 610 and carrier 680 relative to, e.g., a thermal processing system used to thermally cycle materials in the sample process chambers 650. Alignment may also be used in connection with a detection system for detecting the presence or absence of a selected analyte in the process chambers 650.

The carrier 680 may include various features such as openings 682 that are preferably aligned with the process chambers 650 of the sample processing device 610. By providing openings 682, the process chambers 650 can be viewed through the carrier 680. One alternative to providing the openings 682 is to manufacture the carrier 680 of a material (or materials) transmissive to electromagnetic radiation in the desired wavelengths. As a result, it may be possible to use a carrier 680 that is continuous over the surface of the sample processing device 610, i.e., a carrier with no openings formed therethrough for access to the process chambers 650.

Figure 17:
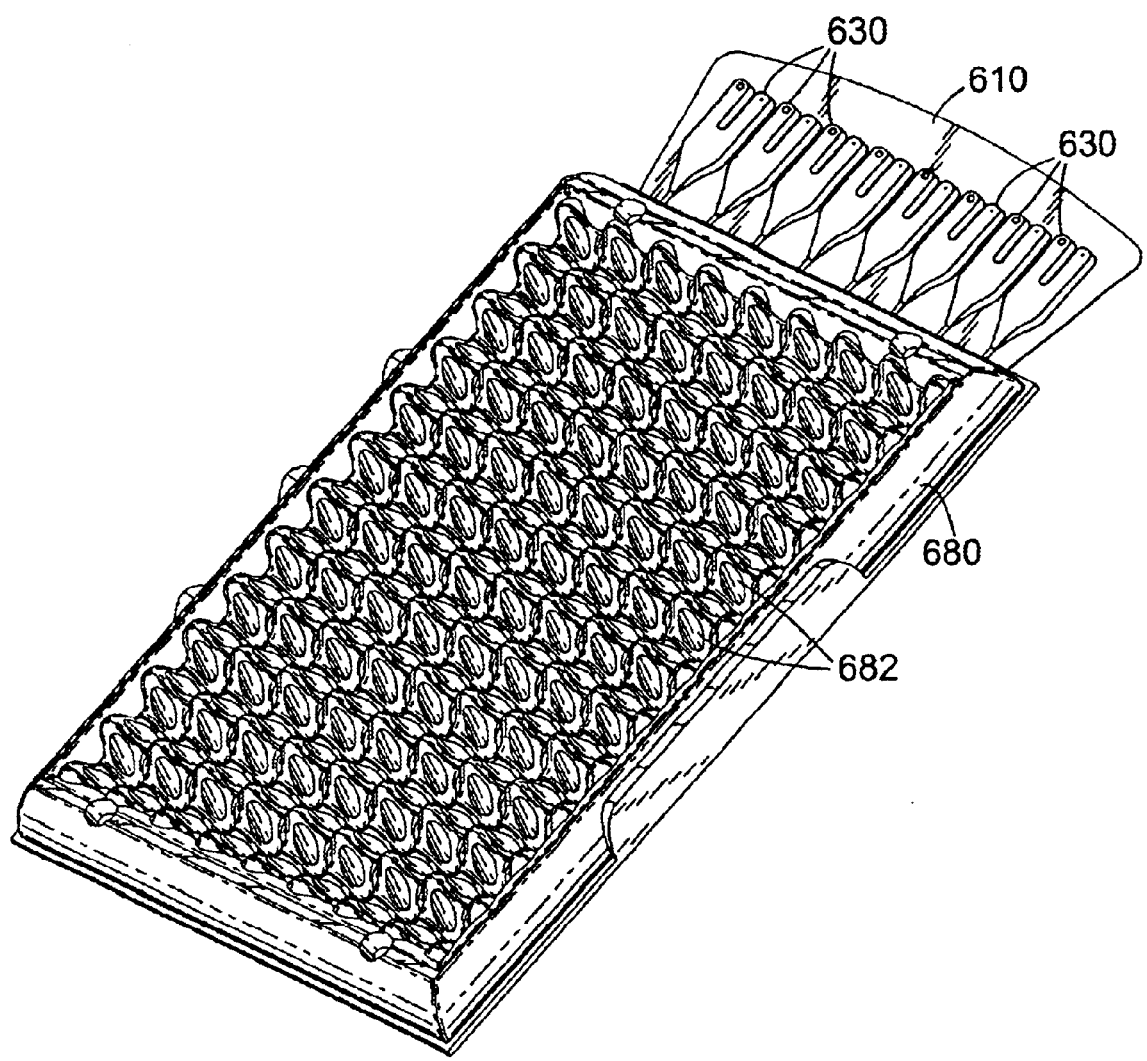
FIG. 17 is a perspective view of the assembly of FIG. 16 as assembled.

The sample processing device 610 and carrier 680 are depicted attached in FIG. 17, where it can be seen that the loading chambers 630 may preferably extend beyond the periphery of the carrier 680. As such, the portion of the sample processing device 610 containing the loading structures 630 may be removed from the remainder of the sample processing device 610 after distributing the sample material to the process chambers 650.

Figure 16:
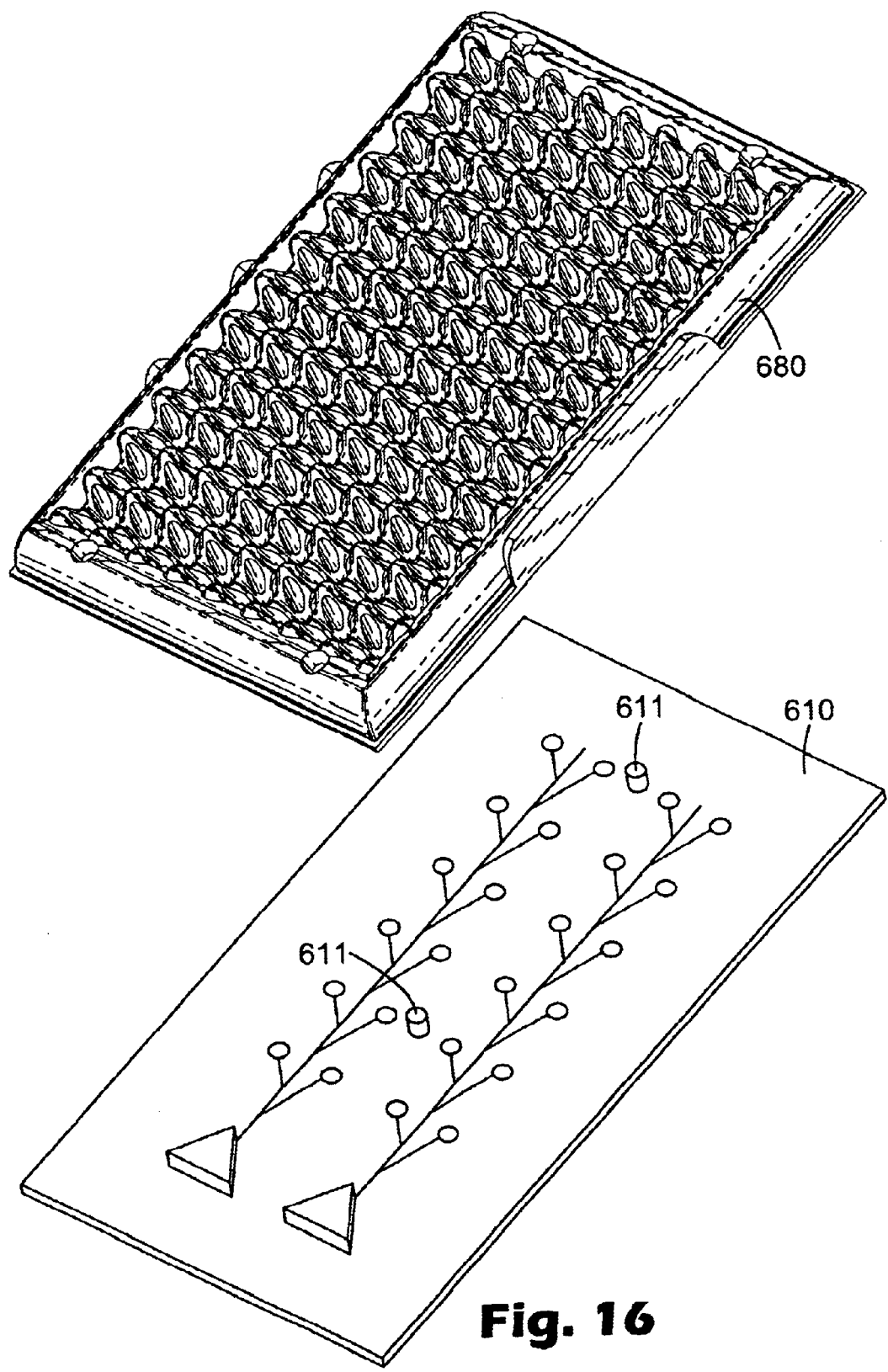
FIG. 16 is an exploded perspective view of an assembly including a sample processing device and a carrier.

The carrier 680 illustrated in FIGS. 16 and 17 may also provide advantages in the sealing or isolation of the process chambers 650 during and/or after loading of sample materials in the process chambers 650.

Figure 18:
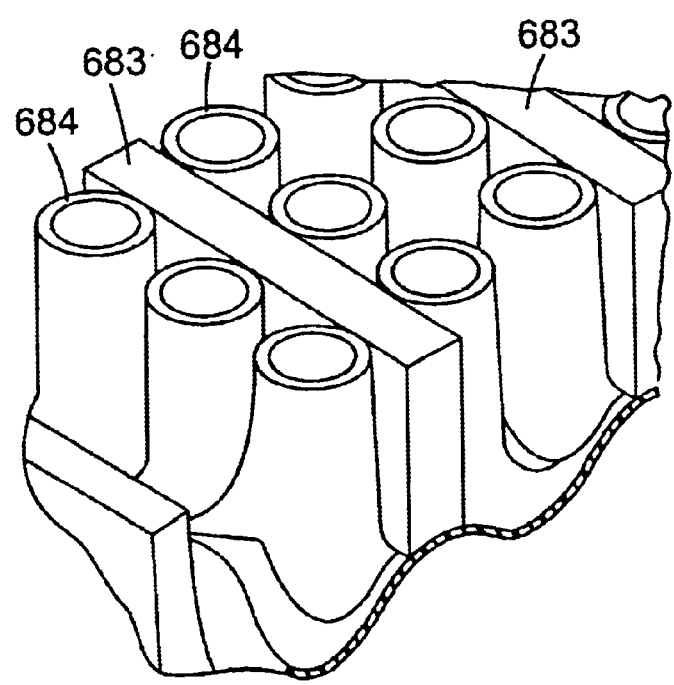
FIG. 18 is an enlarged view of a portion of a carrier depicting one set of main conduit support rails and collars useful in isolating the process chambers on a sample processing device of the present invention.

FIG. 18 is an enlarged view of a portion of the bottom surface of the carrier 680, i.e., the surface of the carrier 680 that faces the sample processing device 610. The bottom surface of the carrier 680 includes a number of features including main conduit support rails 683 that preferably extend along the length of the main conduits 640 in the associated sample processing device 610. The support rails 683 may, for example, provide a surface against which the main conduits 640 of the sample processing device 610 may be pressed while the conduit 640 is deformed to isolate the process chambers 650 and/or seal the conduits 640 as discussed above.

In addition to their use during deformation of the main conduits 640, the support rails 683 may also be relied on during, e.g., thermal processing to apply pressure to the conduits 640. Furthermore, the use of support rails 683 also provides an additional advantage in that they provide for significantly reduced contact between the sample processing device 610 and the carrier 680 while still providing the necessary support for sealing of the main conduits 640 on device 610.

The importance of reducing contact between the carrier 680 and device 610 may be particularly important when the assembly is to be used in thermal processing of sample materials (e.g., polymerase chain reaction, etc.). As such, the carrier 680 may be characterized as including a carrier body that is spaced from the sample processing device 610 between the main conduits 640 when the support rails 683 are aligned with the main conduits 640. The voids formed between the carrier body and the sample processing device 610 may be occupied by air or by, e.g., a compressible and/or thermally insulating material.

Also depicted in FIG. 18 are a number of optional compression structures 684 which, in the depicted embodiment, are in the form of collars arranged to align with the process chambers 650 on the sample processing device 610. The collars define one end of each of the openings 682 that extend through the carrier 680 to allow access to the process chambers 650 on sample processing device 610. The compression structures 684, e.g., collars, are designed to compress a discrete area of the device proximate each of the process chambers 650 on the sample processing device 610 when the two components (the sample processing device 610 and the carrier 680) are compressed against each other.

That discrete areas of compression may provide advantages such as, e.g., improving contact between the device 610 and the thermal block proximate each of the process chambers. That improved contact may enhance the transfer of thermal energy into and/or out of the process chambers. Further, the improvements in thermal transmission may be balanced by only limited thermal transmission into the structure of the carrier 680 itself due, at least in part, to the limited contact area between the sample processing device 610 and the carrier 680.

Another potential advantage of selectively compressing discrete areas of the device 610 is that weakening of any adhesive bond, delamination of the adhesive, and/or liquid leakage from the process chambers 650 may be reduced or prevented by the discrete areas of compression. This advantage may be particularly advantageous when using compression structures in the form of collars or other shapes that surround at least a portion of the process chambers on the sample processing device.

The collars in the depicted embodiment are designed to extend only partially about the perimeter of the process chambers 650 and are not designed to occlude the feeder conduit entering the process chamber 650. Alternatively, however, collars could be provided that are designed to occlude the feeder conduits, thereby potentially further enhancing isolation between the process chambers during thermal processing of sample materials.

The collars 684 may optionally provide some reduction in cross-talk between process chambers 650 by providing a barrier to the transmission of electromagnetic energy (e.g., infrared to ultraviolet light) between the process chambers 650 during processing and/or interrogation of the process chambers 650. For example, the collars 684 may be opaque to electromagnetic radiation of selected wavelengths. Alternatively, the collars 684 may merely inhibit the transmission of electromagnetic radiation of selected wavelengths by diffusion and/or absorption. For example, the collars 684 may include textured surfaces to enhance scattering, they may include materials incorporated into the body of the collar 684 and/or provided in a coating thereon that enhance absorption and/or diffusion.

The carrier 680 may also preferably include force transmission structures to enhance the transmission of force from the upper surface of the carrier 680 (i.e., the surface facing away from the sample processing device) to the compression structures (in the form of collars 684 in the illustrative embodiment) and, ultimately, to the sample processing device itself.

Figure 19:
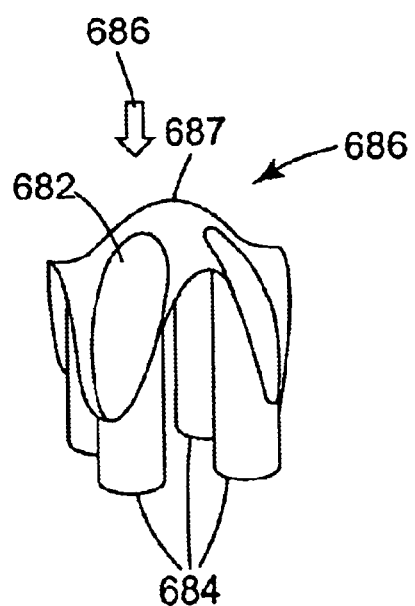
FIG. 19 is a partial cross-sectional view of a portion of a carrier illustrating one example of a force transfer structure useful within the carrier.

FIG. 19 depicts a portion of one illustrative embodiment of one force transmission structure. The force transmission structure is provided in the form of an arch 685 that includes four openings 682 and is operably attached to collars 684. The force transmission structure defines a landing area 687 located between the openings 682 and connected to the collars 684 such that a force 686 applied to the landing area 687 in the direction of the sample processing device is transmitted to each of the collars 684, and, thence, to the sample processing device (not shown). In the depicted embodiment, the landing areas are provided by the crowns of the arches 685.

It is preferred that the arch 685 transmit the force evenly between the different collars 684 attached to the arch 685, which are essentially provided as hollow columns supporting the arch 685 (by virtue of openings 682). This basic structure is repeated over the entire surface of the carrier 680 as seen in, e.g., FIG. 16.

Advantages of providing landing areas on the force transmission structures include the corresponding reduction in contact between the carrier 680 and a platen or other structure used to compress the sample processing device using the carrier 680. That reduced contact can provide for reduced thermal transmission between the carrier 680 and the platen or other structure used to compress the sample processing device. In addition, the force transmission structures and corresponding compression structures on the opposite side of the carrier may all contribute to reducing the amount of material in the carrier 680, thereby reducing the thermal mass of the carrier 680 (and, in turn, the assembly of carrier 680 and sample processing device).

Figure 19A:
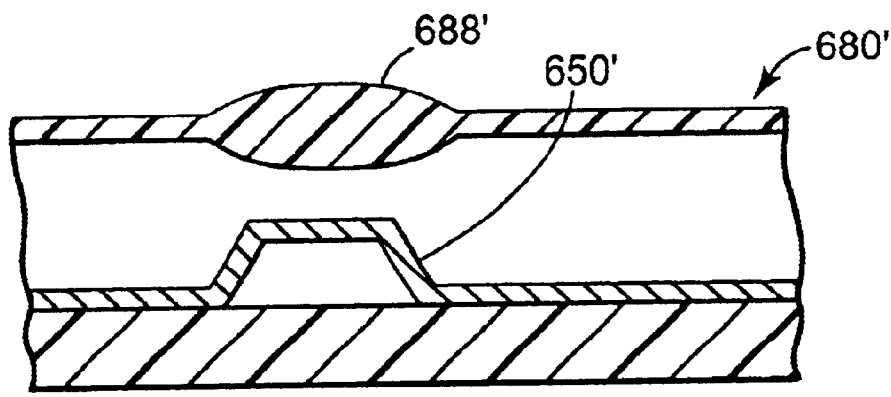
FIG. 19A is a partial cross-sectional view of a carrier and sample processing device assembly including an optical element in the carrier.

FIG. 19A illustrates another optional feature of carriers used in connection with the present invention. The carrier 680' is depicted with an optical element 688', e.g., a lens, that may assist in focusing electromagnetic energy directed into the process chamber 650' or emanating from the process chamber 650'. The optical element 688' is depicted as integral with the carrier 680', although it should be understood that the optical element 688' may be provided as a separate article that is attached to the carrier 680'.

Figure 19B:
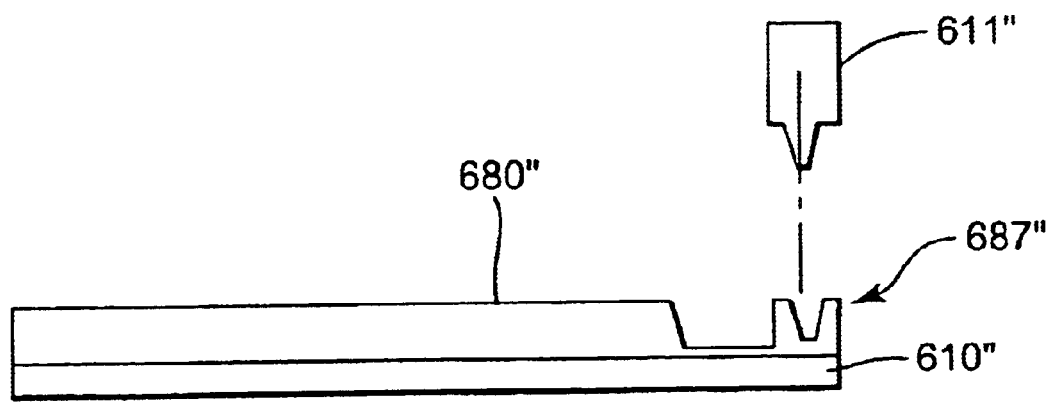
FIG. 19B depicts a carrier and sample processing device assembly including an alignment structure for a sample processing delivery device.

FIG. 19B depicts yet another optional feature of carriers used in connection with the present invention. The carrier 680" includes an alignment structure 687" that may be used to assisting guiding a pipette 611" or other sample material delivery device into the appropriate loading structure on the sample processing device 610". The alignment structure 687" may preferably be removed with the loading structures on the sample processing device 610" as described herein. The alignment structure 687" may be generally conical as depicted to guide the pipette 611" if it is slightly off-center from an inlet port into the loading structure on sample processing device 610".

Figure 20:
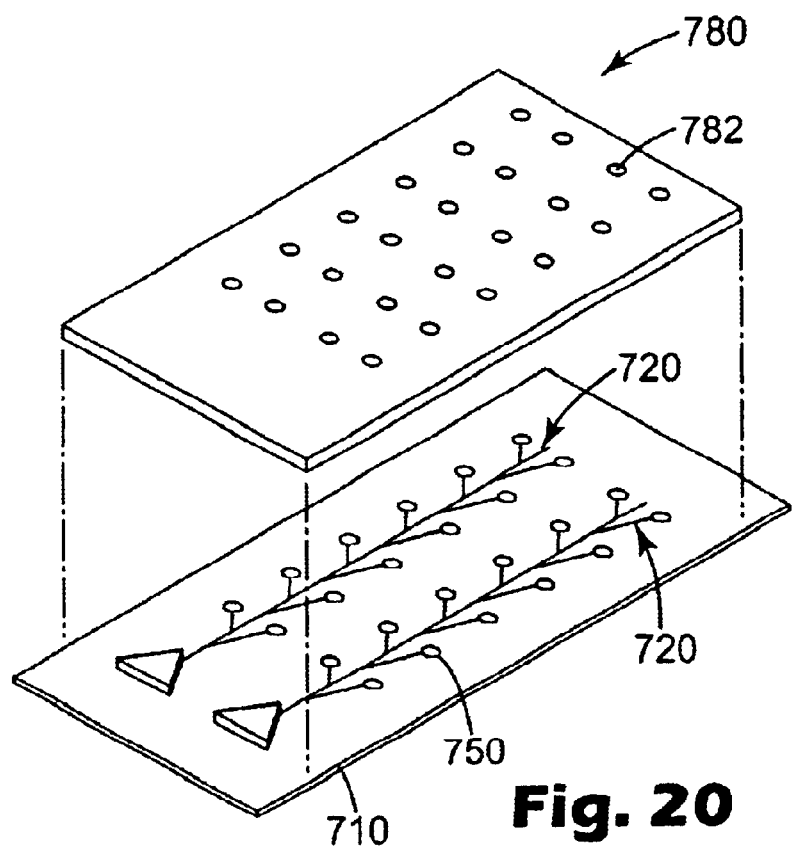
FIG. 20 is an exploded perspective view of an alternative sample processing device and carrier assembly according to the present invention.

As an alternative the molded carrier depicted in FIGS. 16–19, it may be possible to use a carrier in the form of a sheet of material in contact with one side of the sample processing device. FIG. 20 is an exploded view of one illustrative sample processing device 710 and a carrier 780 that may be used in connection with the sample processing device 710.

The sample processing device 710 includes a set of process arrays 720, each of which includes process chambers 750 that, in the depicted sample processing device 710, are arranged in an array on the surface of the sample processing device 710. The carrier 780 includes a plurality of openings 782 formed therein that preferably align with the process chambers 750 when the sample processing device 710 and carrier 780 are compressed together.

The carrier 780 may be manufactured of a variety of materials, although it may be preferred that the carrier be manufactured of a compressible material, e.g., a sheet of compressible foam or other substance. In addition to compressibility, it may be preferred that the compressible material also exhibit low thermal conductivity, low thermal mass, and low compression set, particularly at the temperatures to which the sample processing device will be subjected. One class of suitable foams may include, e.g., silicone based silicone foams.

If the carrier 780 is manufactured of compressible material, there may be no need to provide relief on the surface of the carrier 780 facing the sample processing device 710 to prevent premature occlusion of the conduits in the process arrays 720. If, however, the carrier 780 is manufactured of more rigid materials, it may be desirable to provide some relief in the surface of the carrier 780 for the conduits in the process arrays 720.

Similar to the carrier 680 described above, a carrier 780 such as that depicted in FIG. 20 may also provide for selective compression of the sample processing devices by not compressing the sample processing devices in the areas occupied by the process chambers 750 (due to the absence of material located above the process chambers 750). As a result, the carrier 780 may also provide advantages in that weakening of the adhesive bond, delamination of the adhesive, and/or liquid leakage from the process chambers 750 may be reduced or prevented by the compression provided to the sample processing device 710 outside of the process chambers 750. In addition, thermal leakage from, e.g., a thermal block against which the assembly is urged, may be reduced if the material of the carrier 780 has desirable thermal properties (e.g., low thermal mass, low thermal conductivity, etc.).

The openings 782 may optionally provide some protection reduction in cross-talk between process chambers 750 by providing a barrier to the transmission of electromagnetic energy (e.g., light) between the process chambers 750 during processing and/or interrogation of the process chambers 750. For example, the carrier 780 may be opaque to electromagnetic radiation of selected wavelengths. Alternatively, the carrier may merely inhibit the transmission of electromagnetic radiation of selected wavelengths by diffusion and/or absorption. For example, the openings 782 may include textured surfaces to enhance scattering, the carrier 780 may include materials incorporated into the body of the carrier 780 and/or provided in a coating thereon that enhance absorption and/or diffusion of selected wavelengths of electromagnetic energy.

The carriers described above in connection with FIGS. 16–20 may be fixedly attached to the sample processing device or they may be separate from the sample processing device. If separate, the carriers may be removably attached to or brought into contact with each sample processing device in a manner that facilitates removal from an sample processing device without significant destruction of the carrier. As a result, such carriers may be used with more than one sample processing device. Alternatively, however, the carriers may be firmly affixed to the sample processing device, such that both components are discarded after use. In some instances, the carrier may be attached to the system used to process the sample processing devices, e.g., the platen of a thermocycling system, such that as an sample processing device is loaded for thermal processing, the carrier is placed into contact with the sample processing device.

Both of the carriers described above are examples of means for selectively compressing the first side and second side of a sample processing device together about each process chamber. It is preferred that the compression occur simultaneously about each process chamber. Many other equivalent structures that accomplish the function of selectively compressing the first side and second side of a sample processing device together about each process chamber may be envisioned by those of skill in the art. In some embodiments, it may be preferred that the means for selectively compressing applies compressive force over substantially all of the sample processing device outside of the process chambers (e.g., the resilient carrier 780). In other embodiments, it may be preferred that the means for selectively compressing applies compressive forces in only a localized area about each of the process chambers in the sample processing device (e.g., carrier 680 with its associated collars).

Figure 20A:
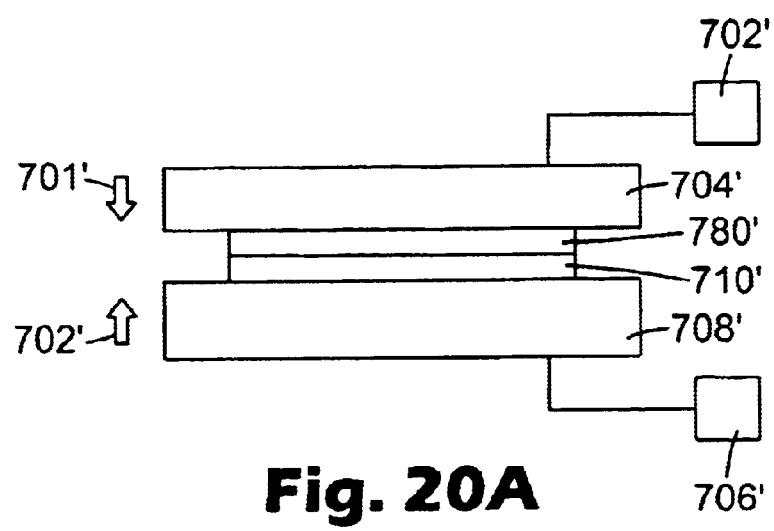
FIG. 20A is a block diagram of one thermal processing system that may be used in connection with the sample processing devices of the present invention.

Any system incorporating a means for selectively compressing may attach the means for selectively compressing to the sample processing device or to a platen or other structure that is brought into contact with the sample processing device during processing. FIG. 20A depicts one thermal processing system that may be used in connection with the sample processing devices of the present invention in a block diagram format. The system includes an sample processing device 710' located on a thermal block 708'. The temperature of the thermal block 708' is preferably controlled by a thermal controller 706'. On the opposite side of the sample processing device 710', the means for selectively compressing (in the form of carrier 780') is located between the sample processing device 710' and a platen 704'. The platen 704' may be thermally controlled (if desired) by a thermal controller 702' (that may, in some instances, be the same as controller 706' controlling the temperature of the thermal block 708'). The sample processing device 710' and the means for selectively compressing 780' are compressed between the platen 704' and thermal block 708' as indicated by arrows 701' and 702' during thermal processing of the sample processing device 710'.

FIGS. 21–25 depict various aspects of one apparatus that may be used to isolate the process chambers in a sample processing device of the present invention, where that isolation is achieved by occluding the main conduits connecting the loading structures to the process chambers.

Figure 21:
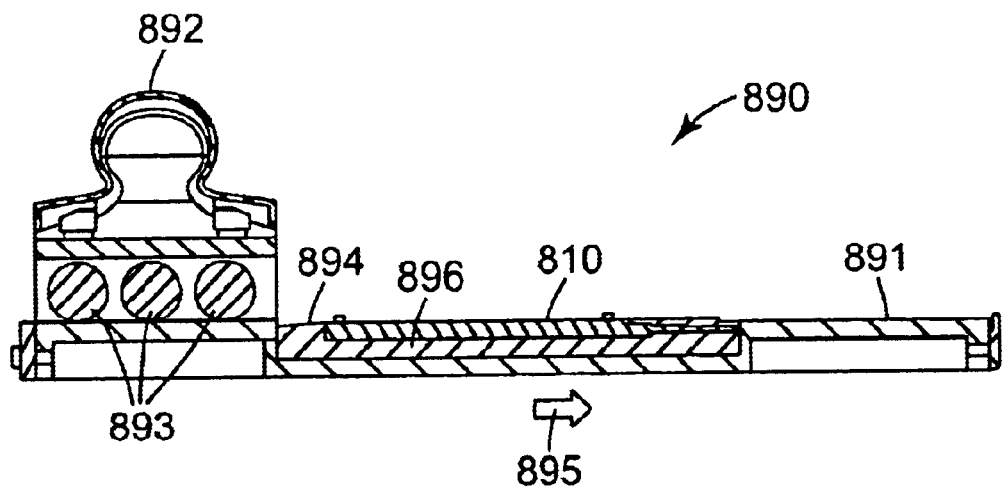
FIG. 21 is a schematic diagram of one sealing apparatus that may be used in connection with the present invention.
Figure 22:
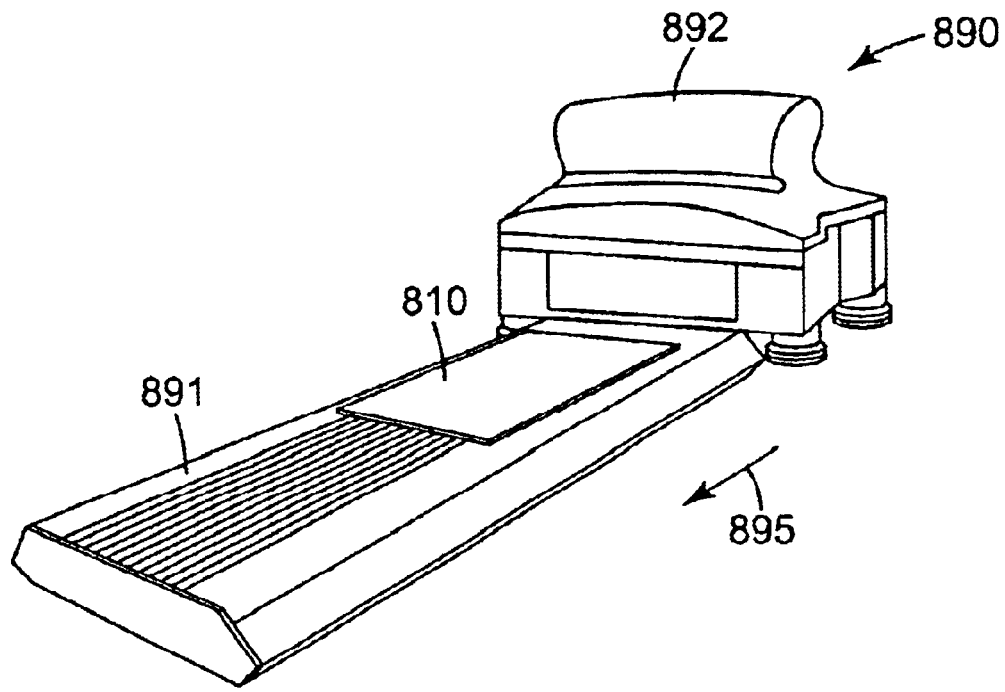
FIG. 22 is a perspective view of the apparatus of FIG. 21.

FIG. 21 is a schematic diagram of one sealing apparatus 890 that may be used in connection with the sample processing devices of the present invention. The sealing apparatus 890 is depicted with a sample processing device 810 loaded within bed 894. The depicted sealing apparatus 890 can be used to seal or occlude the process arrays in a sample processing device 810 loaded in bed 894. A device such as sealing apparatus 890 may be particularly useful with sample processing devices that include a set of parallel main conduits that can be sealed or occluded by deforming a portion of the sample processing devices as discussed above in various embodiments.

The sealing apparatus 890 includes a base 891 and a bridge 892 that is traversed across a portion of the base 891 in the direction of arrow 895. The bridge 892 includes, in the depicted embodiment, a series of rollers 893 designed to seal or occlude portions of the process arrays by compressing the sample processing device within the bed 894.

The bed 894 may be constructed of a variety of materials, although it may be preferred that the bed 894 include a layer or layers of a resilient or elastomeric material that provides some support to the sample processing devices and that can also providing some compressibility in response to the forces generated as the bridge 892 is traversed across the sample processing device 810.

The bed 894 preferably includes a cavity 896 into which the sample processing device 810 is situated such that the upper surface of the sample processing device 810 is generally coplanar with the remainder of the bed 894. The cavity 896 may be relatively simple in shape where the sample processing device 810 includes a carrier as described above. In those situations, the carrier may preferably include main conduit support rails that are located underneath each of the main conduits and support the main conduits as the rollers 893 traverse the sample processing device 810. If no carrier is present, or if the carrier used does not include support rails for the main conduits, it may be possible to provide a shaped bed 894 that includes support rails for the portions of the sample processing device to be compressed by the rollers 893. Even if a carrier is present as a part of the sample processing device 810, portions of the sample processing device 810 may be unsupported by the carrier, such as the portion including the loading channels (see, e.g., FIG. 17). In those situations, it may be preferred that the bed 894 include shaped portions that provide support to the main conduits outside of the carrier such that sealing or occlusion of those portions of the main conduits may be effectively performed using the apparatus 890.

Sealing of the main conduits in the sample processing device 810 is accomplished by traversing the bridge 892 across the sample processing device 810 in the direction of arrow 895. As the bridge 892 is moved, the rollers 893 rotated across the surface of the sample processing device 810 to effect the sealing of the main conduits in the sample processing device 810. Although the sealing apparatus 890 is depicted as including a series of rollers 893, it will be understood that the rollers could be replaced by other structural members such as pins, wires, styli, blades, etc., that, rather than rolling across the sample processing device 810, are drawn across the sample processing device 810 in a sliding motion. It may, however, be preferred that a rolling structure be used for sealing the main conduits in sample processing device 810 to reduce the amount of friction generated during the sealing process.

The rollers 893 (or other sealing structures) may be mounted within the bridge 892 in a variety of manners. For example, the rollers 893 may be fixedly mounted within the bridge, such that their height relative to the base 810 is fixed. Alternatively, one or more of the rollers 893 may be mounted in a suspension apparatus such that the height of the rollers 893 can vary in response to forces generated during sealing. If suspended, the portions of the rollers responsible for sealing each of the main conduits in a sample processing device 810 may be individually suspended such that each portion of the roller can move independently of other portions of the roller. As an alternative to individually suspended portions of the rollers 893, it may be preferred that each roller 893 depicted in FIG. 21 be provided as a one-piece cylindrical unit with structures formed on its surface that provide the desired sealing capabilities.

Figure 23:
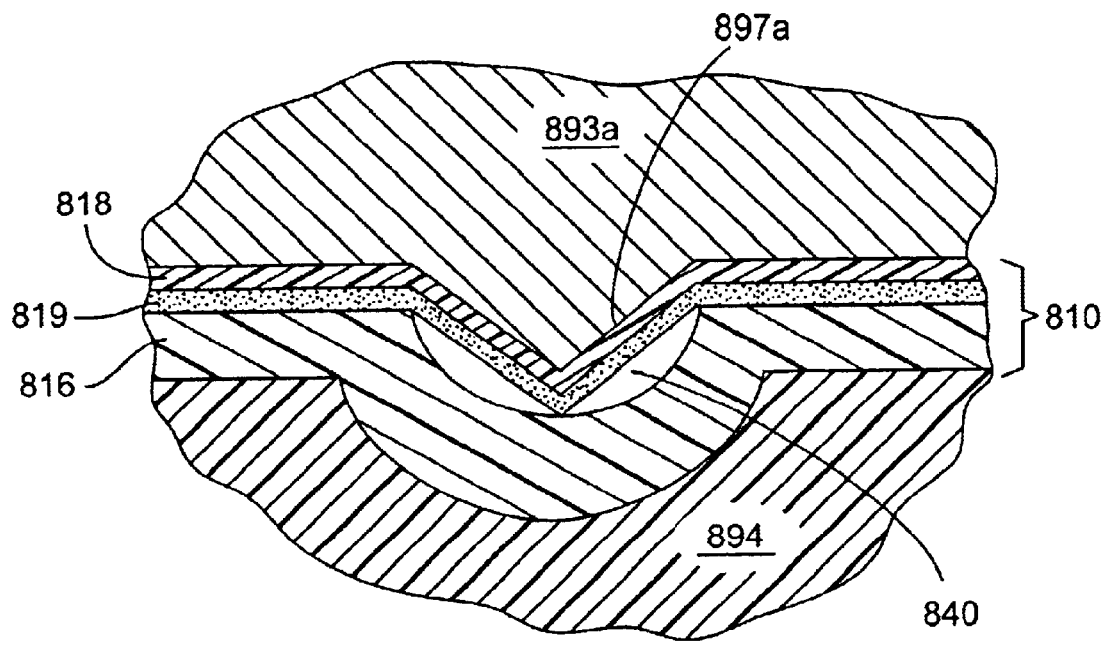
FIGS. 23–25 depict profiles of various sealing structures used to occlude conduits in connection with the apparatus of FIGS. 21 & 22.
Figure 24:
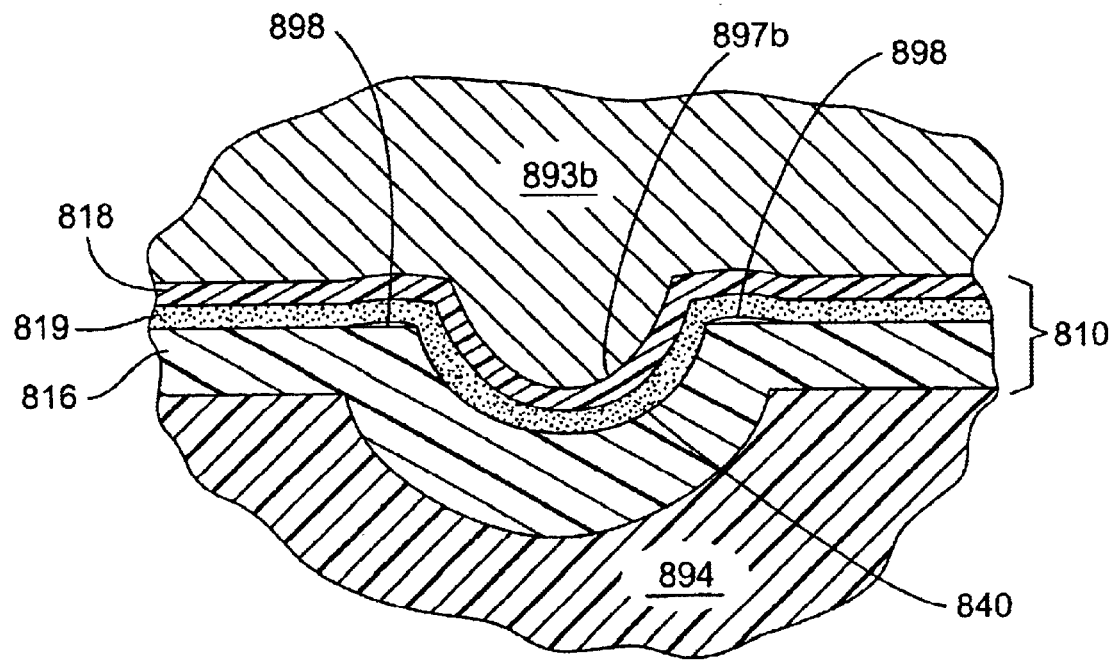
Figure 25:
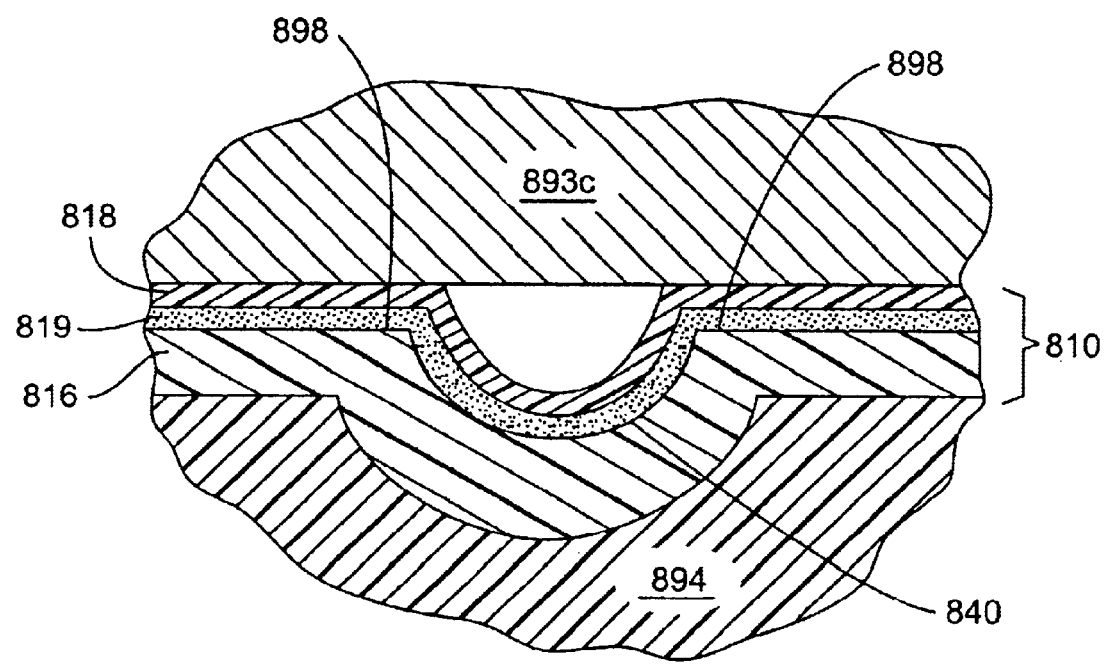

FIGS. 23 through 25 depict enlarged partial cross-sectional views of the sealing of main conduits using a device such as sealing apparatus 890. As depicted in the series of FIGS. 23–25, it may be preferred that the sealing process be accomplished with a series of rollers (or other sealing structures as discussed above) that occlude the process array conduits in a sequential manner. Referring to FIG. 23, for example, the roller 893a (only a portion of which is depicted in the cross-sectional view of FIG. 23) may include a ridge 897a that forces/deforms a portion of the second side 818 of sample processing device 810 into the main conduit 840. In the depicted view, the main conduit 840 includes sample material located therein. Further, the main conduit 840 is supported against the forces applied by the roller 893 by a shaped structure formed in bed 894. If this cross-sectional view were, alternatively, taken along a line running through a carrier, the main conduit may, instead be supported by a main conduit support rail as described above in connection with the sample processing device/carrier assemblies.

The result of the compression is that a portion of the second side 818 and associated adhesive 819 are forced into conduit 840 (towards the first side 816) of the sample processing device 810. The deformation of the second side 818 may preferably result in occlusion of the main conduit that is partial. The partial occlusion may preferably be accompanied by adhesion of the first side 816 to the second side 818 using adhesive 819 within the main conduit 840. In some instances, this partial occlusion of the main conduit 840 may be sufficient to isolate the various process chambers located along the main conduit 840. As a result, the view depicted in FIG. 23 may be one of a sealed processed array in some instances.

It may, however, be preferred that the main conduit 840 be more occluded than that depicted in FIG. 23. FIG. 24 depicts a second roller 893b and associated ridge 897b That presents a more rounded profile than the profile of ridge 897a depicted in FIG. 23. The more rounded profile of ridge 897b may be shaped to have a more complementary fit with the main conduit 840 of sample processing device 810. As a result of that more complementary shape, the ridge 897b may preferably cause substantially complete occlusion of the main conduit 840, thereby adhering the first side 816 together with the second side 818 within the main conduit 840.

Where the second side 818 is deformed to occlude the main conduit 840 and the sample processing device is constructed using an adhesive between the first side 816 and the second side 818, deformation of the sample processing device 810 may result in some delamination between the first side 816 and the second side 818, particularly along the edges 898 of the main conduit 840 as depicted in FIG. 24. Thus, in some instances, it may be desirable to perform a secondary relamination operation after occluding the main conduits.

FIG. 25 depicts one mechanism that may be used to address the delamination in the form of a roller 893c that is designed to compress the first side 816, second side 818, and adhesive 819 against the bed 894 to relaminate the sample processing device along the edges 898 of the main conduit 840.

The rollers or other sealing structures, e.g., pins, blades, etc., may be manufactured of a variety of materials depending on the construction of the sample processing devices to be sealed. The sealing structures may, for example, be constructed of elastomeric coated rollers or other structures, they may be coated with low surface energy materials to reduce friction, they may be constructed entirely of rigid materials (e.g., metals, rigid polymers, etc.). Further, where multiple sealing structures are used (such as the three rollers 893 depicted in FIG. 21), the different sealing structures may be constructed of a variety of materials, some rigid, some resilient, some including rigid and resilient portions. For example, the roller 893b may preferably be constructed of rigid base roll with only the ridge 897b constructed of resilient material to better conform to the shape of the main conduit 840. Alternatively, the base roll may be resilient while the ridge 897b is constructed of rigid materials.

Some Alternative Constructions

FIGS. 26A–26F depict some additional optional features that may be included as a part of the deformable seal used to close the main conduits and/or the feeder conduits (if any) in sample processing devices of the present invention. One optional feature includes a seal structure 935 and a conformable seal element 936 located in area 934 of conduit 932. It will be understood that although both features are illustrated together in FIGS. 3A and 3B, either one may be provided alone to enhance closure of the conduit 932 in area 934.

The seal structure 935 may be provided as illustrated, where it is integral with the first side 950. Alternatively, it could be provided as an additional element attached to the substrate 152 or the adhesive 154 after it is attached to the substrate 152. Regardless of its exact construction, it is preferred that the seal structure extend into the conduit 932 to provide a structure against which the second side 960 can be pressed to seal the distribution channel 932. By providing a discontinuity in the otherwise preferably uniform cross-section of the conduit 932, the seal structure 935 may enhance occlusion of the conduit 932. Furthermore, although only one seal structure 935 is illustrated, multiple seal structures may be provided, e.g., in the form of aligned ridges. It may be preferred that the seal structure extend across the full width of the conduit 932 Additionally, the seal structure may take a variety of shapes, with the illustrated rounded ridge being only one example. Other potential shapes may include, but are not limited to, rectangular ridges, triangular ridges, etc.

Like the seal structure 935, the conformable seal element 936 may be provided to enhance occlusion of the conduit 932 in the area 934 and preferably exhibits some conformance in response to the compressive forces used to occlude the conduit 932. That conformability may improve closure of the conduit 932 after the deformation force is removed. When used with a seal structure 935 that provides a discontinuity on the opposing surface of the conduit 932, the conformable seal element 936 may be even more effective at closing the conduit 932 as it conforms to the seal structure 935 (see FIG. 26B).

The conformable seal element 936 may be provided in a variety of forms. For example, the conformable seal element 936 may be provided as a discrete structure, e.g., an elastomer such as silicone, a conformable pressure sensitive adhesive, a wax, etc. Alternatively, the conformable seal element 936 may be provided within the various sub-layers forming the side 960 of the device 910. In yet another alternative, the conformable seal element 936 may be provided as a thickened area of the one of the layers within the side 960, e.g., layer 962, 964, or 966.

Figure 26A:
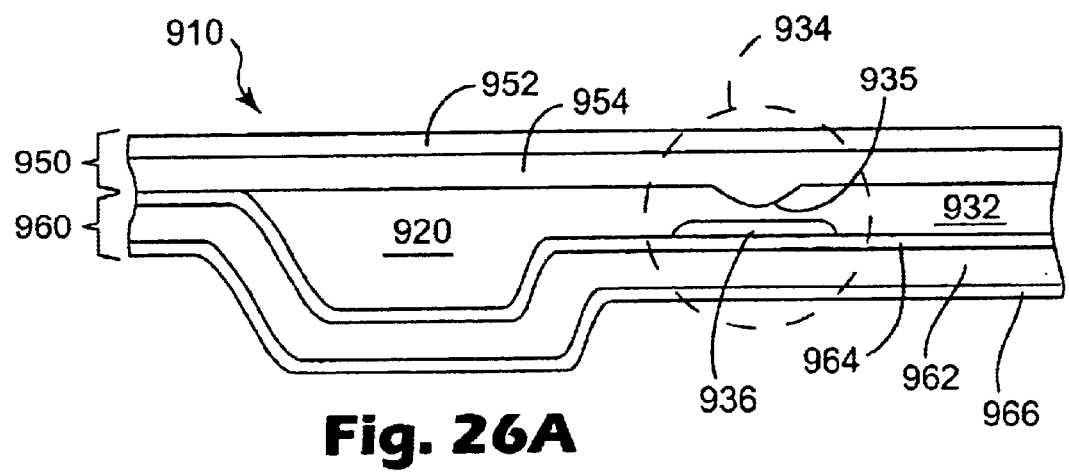
FIGS. 26A–26F depict various seal structures useful in connection with sample processing devices of the present invention.
Figure 26B:
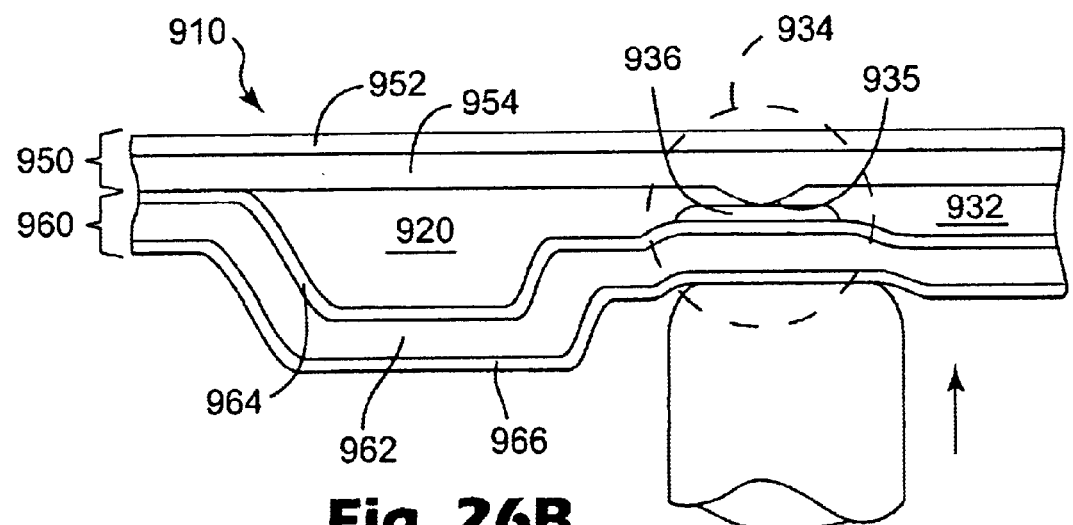
Figure 26C:
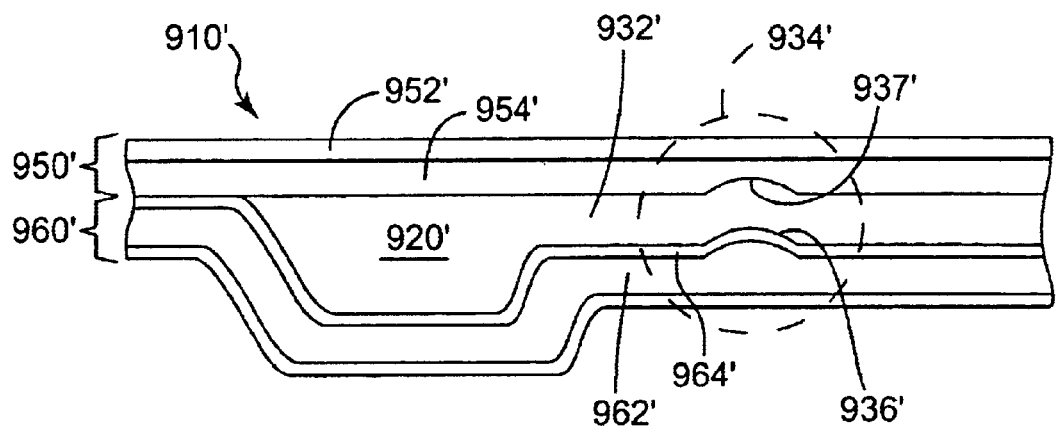
Figure 26D:
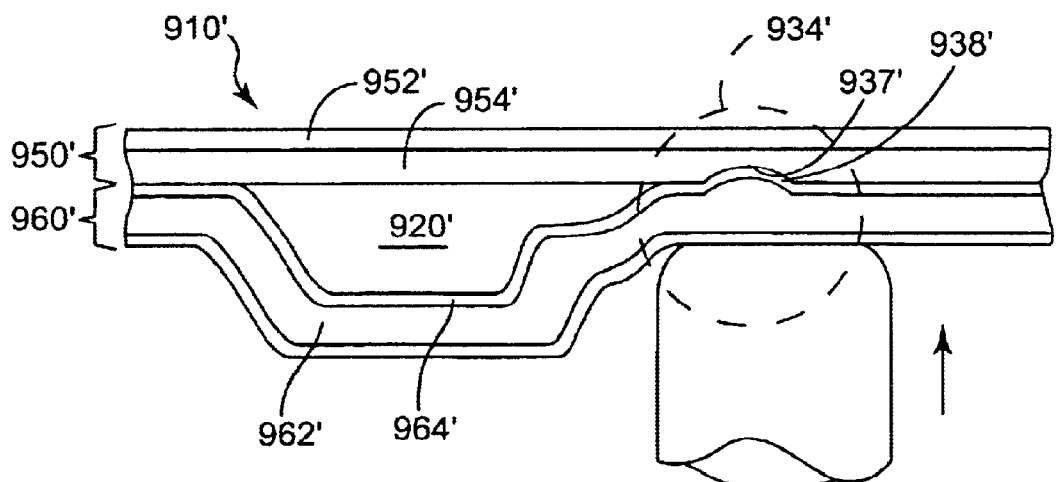

FIGS. 26C and 26D illustrate an alternative area 934' of conduit 932' that includes other optional features used to close conduit 932' in fluid communication with process chamber 920'. The area 934' includes complementary mating seal structures 937' and 938' formed on the opposing sides 950' and 960' of the conduit 932'. When deformed during closure of the conduit 932', the mating structures 937' and 938' may provide a more tortuous fluid path, thereby improving closure of the conduit 932'.

In yet another alternative, the seal structure 938' provided on the second side 960' may be provided alone, with the adhesive 954' being of a uniform thickness. The adhesive 954' may, however, exhibit some deformation as a result of the compressive force used to close the conduit 932' and that deformation may improve occlusion of the conduit 932'. In addition, the adhesive 954' may preferably adhere to the seal structure 938', thereby further improving closure of the conduit 932'.

Figure 26E:
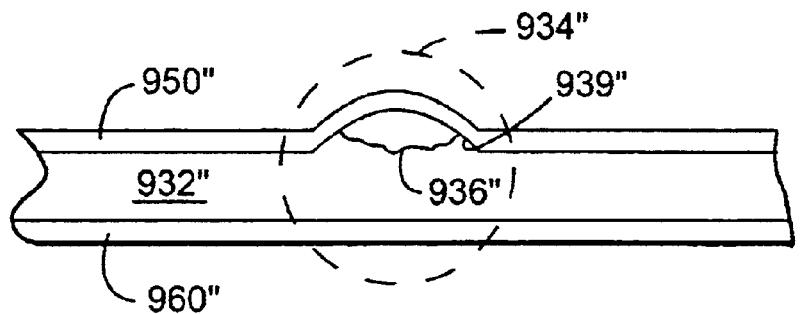
Figure 26F:
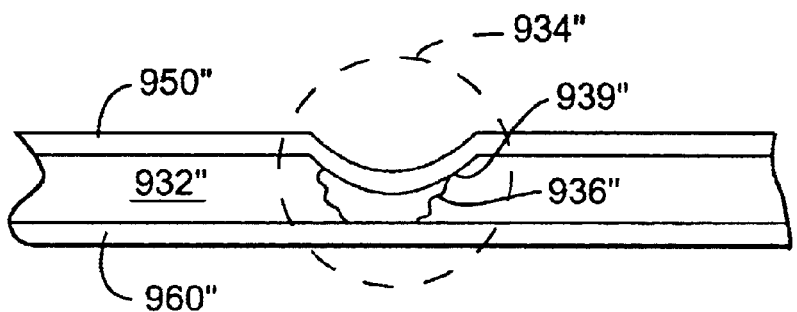

Yet another illustrative structure that may enhance occlusion of the conduit 932" is depicted area 934" in FIGS. 26E and 26F. The structure in area 934" includes a cavity 939" formed in the first side 950" of the device. The cavity 939" may preferably include a conformable seal element 936" that is forced against the opposing side of the conduit 932" when the cavity 939" is depressed. The conformable seal element 936" may be, e.g., an elastomer, a pressure sensitive adhesive, a wax, etc. The cavity 939" may preferably be dome-shaped such that pressure causes it to extend into the conduit 932" as illustrated in FIG. 26F.

One potential advantage of the structures in area 934" is that, before closure, no portion of the structures in area 934" extends into the conduit 932" to impede or disrupt flow therethrough. Another potential advantage of the structures illustrated in FIGS. 26E and 26F is that registration of the two sides 950" and 960" may not be required during bonding of the two major sides because the structures are all located on one side of the device.

As an alternative to the structure shown in FIGS. 26E and 26F, the conformable seal element may be provided as a layer of pressure sensitive adhesive on the second major side 960" against which the cavity 939" is forced upon closure of the conduit 932".

Figure 27A:
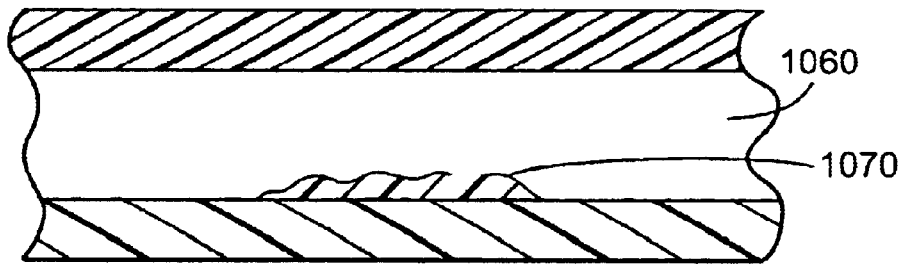
FIGS. 27A & 27B depict one seal including an expandable material used to occlude a conduit in a sample processing device of the present invention.
Figure 27B:
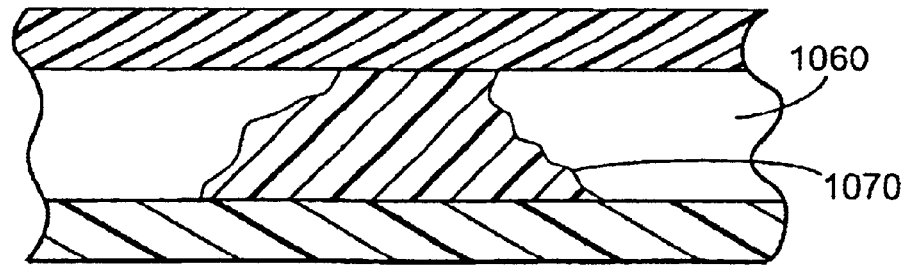

FIGS. 27A & 27B depict yet another potential variation for the deformable seals that may be used to isolate process chambers in sample processing devices of the present invention. The depicted seal structure 1070 may be located along a conduit 1060 (e.g., main conduit or feeder conduit). The seal structure 1070 may be provided in the form of material located along the conduit 1060. When heated above a selected temperature, the material of the seal structure 1070 deforms (in the illustrated case the deformation is in the form of expansion) to partially or completely occlude the conduit 1060. The material used in the seal structure 1070 may be, e.g., polymer that expands to form a foamed polymer. The foaming action may be provided, e.g., by using a blowing agent or supercritical carbon dioxide impregnation.

Where a blowing agent is used in the seal structure 1070, it may be impregnated into the polymer. Examples of suitable blowing agents include, but are not limited to: CELOGEN AZ (available from Uniroyal Corporation, Middlebury, Conn.), EXPANCEL microspheres (Expancel, Sweden), and glycidyl azide based polymers (available from Minnesota Mining and Manufacturing Company, St. Paul, Minn.). When the impregnated polymer is then heated above a selected temperature, the blowing agent generates a gas that causes the polymer to foam and expand and close the seal structure 1070 as depicted in FIG. 27B.

Supercritical foaming may also be used to occlude the conduit 1060 by expanding the seal structure 1070. A polymer may be caused to foam by impregnating the polymer with, e.g., carbon dioxide, when the polymer is heated above its glass transition temperature, with the impregnating occurring under high pressure. The carbon dioxide may be applied in liquid form to impregnate the polymeric matrix. The impregnated material can be fabricated into the valve structure, preferably in a compressed form. When heated the carbon dioxide expands, the structure also deforms by expanding, thereby closing the conduit 1060.

Figure 28A:
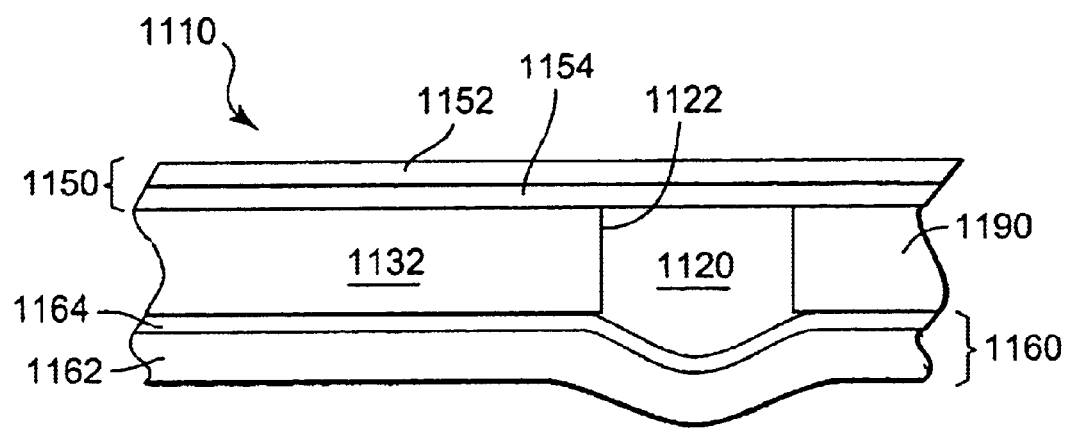
FIGS. 28A & 28B depict an alternative construction for an sample processing device of the present invention including a core located between opposing sides.
Figure 28B:
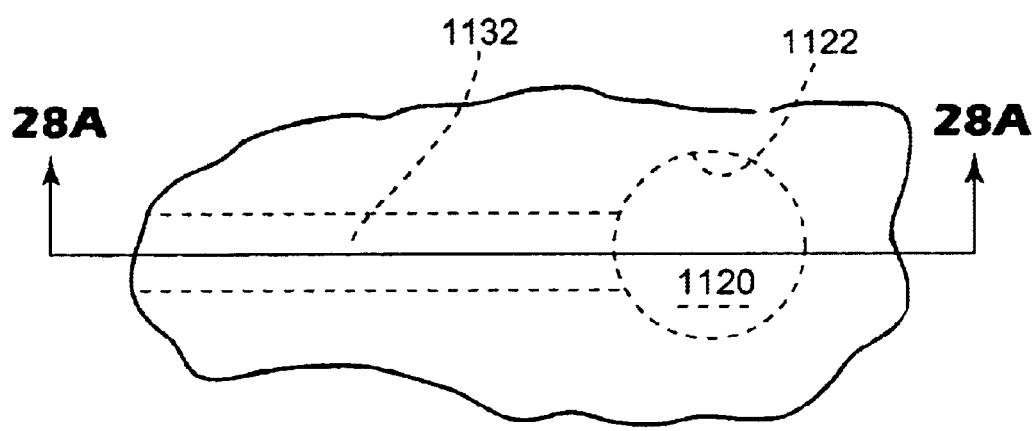

FIGS. 28A and 28B depict one alternative construction for a sample processing device 1110 according to the present invention. The sample processing device 1110 includes a core 1190, a first side 1150 attached to one major surface of the core 1190 and a second side 1160 attached to the other major surface of the core 1190. The second side 1160 preferably includes a metallic layer 1162 and passivation layer 1164 that is located between the metallic layer 1162 and the core 1190.

The core 1190 includes a plurality of voids 1122 formed therein that extend through both major surfaces of the core 1190. The voids 1122, together with the first and second sides 1150 and 1160 define process chambers 1120 of the sample processing device 1110. In addition to the voids 1122, the process chamber volume may further be defined by structures formed in one or both of the sides. For example, the second side 1160 includes structures in the form of depressions that increase the volume of the process chambers 1120.

The core 1190 may also include elongated voids 1134 that form conduits 1132 in fluid communication with the process chambers 1120. The voids 1134 may be formed completely through the core 1190 as are the voids 1122 forming the process chambers 1120 or they may be formed only partially through the thickness of the core 1190.

The core 1190 may be formed of a variety of materials, although it may be preferable to manufacture the core 1190 from polymeric materials. Examples of suitable polymeric materials include, but are not limited to, polypropylene, polyester, polycarbonate, polyethylene, etc. It may further be preferred that the core 1190 be manufactured of materials that are compatible with the reactions and any materials (samples, reagents, etc.) that may be located within the process chambers 1120.

The second side 1160 may be manufactured of materials similar to those used in, e.g., the construction of the sample processing devices described above. The adhesive layers 1154 and 1164 used to connect the sides 1150 and 1160 to the core 1190 may be the same or different. As an alternative to the adhesives, the layers 1154 and/or 1164, or their respective substrates 1152 and/or 1162, may be constructed of materials that are amenable to melt bonding to the core 1190.

Patents, patent applications, and publications disclosed herein are hereby incorporated by reference as if individually incorporated. It is to be understood that the above description is intended to be illustrative, and not restrictive. Various modifications and alterations of this invention will become apparent to those skilled in the art from the foregoing description without departing from the scope of this invention, and it should be understood that this invention is not to be unduly limited to the illustrative embodiments set forth herein.

What is claimed is:

1. A sample processing assembly comprising:
    a sample processing device comprising:
        a body that comprises a first side attached to a second side;
        a plurality of process arrays formed between the first and second sides, wherein each process array of the plurality of process arrays comprises a loading structure, a main conduit comprising a length, a plurality of process chambers distributed along the main conduit, and a deformable seal located between the loading structure and the plurality of process chambers, wherein the main conduit is in fluid communication with the loading structure and the plurality of process chambers;
    a carrier attached to the sample processing device, the carrier comprising:
    a first surface facing the sample processing device and a second surface facing away from the sample processing device;
        a plurality of main conduit support rails proximate the first surface of the carrier, wherein each main conduit of the plurality of process arrays is aligned with one main conduit support rail of the plurality of main conduit support rails; and
        a plurality of openings formed through the first and second surfaces of the carrier, wherein each opening of the plurality of openings is aligned with one process chamber of the plurality of process chambers.

2. An assembly according to claim 1, wherein the carrier further comprises a plurality of compression structures proximate the first surface of the carrier, each compression structure of the plurality of compression structures proximate one process chamber of the plurality of process chambers.

3. An assembly according to claim 1, wherein the carrier further comprises:
    a plurality of compression structures proximate the first surface of the carrier, each compression structure of the plurality of compression structures proximate one process chamber of the plurality of process chambers; and
    a plurality of force transmission structures, each force transmission structure of the plurality of force transmission structures comprising a discrete landing area proximate the second surface of the carrier, and each force transmission structure of the plurality of force transmission structures being operatively connected to a plurality of the plurality of compression structures, wherein a force applied to the landing surface of each force transmission structure is transmitted to the plurality of compression structures operatively connected to the force transmission structure.

4. An assembly according to claim 1, wherein the carrier further comprises a plurality of collars proximate the first surface of the carrier, each collar of the plurality of collars aligned with and proximate to one process chamber of the plurality of process chambers.

5. An assembly according to claim 4, wherein each collar in the plurality of collars diffuses or absorbs electromagnetic radiation of selected wavelengths.

6. An assembly according to claim 1, further comprising a plurality of collars proximate the first surface of the carrier, wherein each opening of the plurality of openings is aligned with one collar of the plurality of collars, and further wherein each collar of the plurality of collars is aligned with one process chamber of the plurality of process chambers.

7. An assembly according to claim 1, further comprising at least one reagent in at least one of the process chambers.

8. An assembly according to claim 1, wherein each process chamber of the plurality of process chambers comprises a volume of about 5 microliters or less.

9. An assembly according to claim 1, wherein the second side of the sample processing device comprises a metallic layer.

10. An assembly according to claim 1, wherein the sample processing device comprises adhesive located between the first side and the second side of the sample processing device.

11. An assembly according to claim 1, wherein the sample processing device comprises pressure sensitive adhesive located between the first side and the second side of the sample processing device.

12. An assembly according to claim 1, wherein, for each process array of the plurality of process arrays, the deformable seal comprises a deformable portion of the second side of the sample processing device.

13. An assembly according to claim 1, wherein, for each process array of the plurality of process arrays, the deformable seal comprises a deformable metallic layer.

14. An assembly according to claim 1, wherein, for each process array of the plurality of process arrays, the deformable seal comprises a deformable portion of the second side of the body, the deformable portion extending along substantially all of the length of the main conduit.

15. An assembly according to claim 1, wherein, for each process array of the plurality of process arrays, the deformable seal comprises adhesive located between the first side and the second side, the adhesive extending along a portion of the length of the main conduit.

16. An assembly according to claim 1, wherein, for each process array of the plurality of process arrays, the deformable seal comprises adhesive located between the first side and the second side, the adhesive extending along substantially all of the length of the main conduit.

17. An assembly according to claim 1, wherein, for each process array of the plurality of process arrays, the deformable seal comprises conformable seal material.

18. An assembly according to claim 1, wherein, for each process array of the plurality of process arrays, the deformable seal comprises expandable seal material.

19. A method of processing sample materials, the method comprising:
   providing a sample processing assembly comprising:
      a sample processing device comprising:
         a body that comprises a first side attached to a second side;
         a plurality of process arrays formed between the first and second sides, wherein each process array of the plurality of process arrays comprises a loading structure, a main conduit comprising a length, and a plurality of process chambers distributed along the main conduit, wherein the main conduit is in fluid communication with the loading structure and the plurality of process chambers;
         a deformable seal located between the loading structure and the plurality of process chambers in each process array of the plurality of process arrays; and
      a carrier attached to the sample processing device, the carrier comprising:
         a first surface facing the sample processing device and a second surface facing away from the sample processing device;
         a plurality of main conduit support rails proximate the first surface of the carrier, wherein each main conduit of the plurality of process arrays is aligned with one main conduit support rail of the plurality of main conduit support rails; and
         a plurality of openings formed through the first and second surfaces of the carrier, wherein each opening of the plurality of openings is aligned with one process chamber of the plurality of process chambers;
   distributing sample material to at least some of the process chambers in each process array of the plurality of process arrays through the main conduit in each of the process arrays;
   closing the deformable seal in each process array of the plurality of process arrays, the closing comprising supporting the main conduit with one of the main conduit support rails while compressing the first side and the second side of the sample processing device together along the main conduit;
   locating the second side of the sample processing device in contact with a thermal block; and
   controlling the temperature of the thermal block while the sample processing device is in contact with the thermal block.

20. A method according to claim 19, wherein closing the deformable seal in each process array of the plurality of process arrays comprises simultaneously closing the deformable seal in each process array of the plurality of process arrays.

21. A method according to claim 19, wherein, for each process array of the plurality of process arrays, closing the deformable seal comprises occluding the main conduit along substantially all of its length.

22. A method according to claim 19, wherein, for each process array of the plurality of process arrays, closing the deformable seal comprises occluding the main conduit along only a portion of its length.

23. A method according to claim 19, wherein, for each process array of the plurality of process arrays, closing the deformable seal comprises occluding the main conduit along substantially all of its length beginning at a point distal from the loading structure and proceeding towards the loading structure, whereby sample material within the main conduit is urged towards the loading structure.

24. A method according to claim 19, wherein, for each process array of the plurality of process arrays, closing the deformable seal comprises occluding only a portion of the length of the main conduit beginning at a point distal from the loading structure and proceeding towards the loading structure, whereby sample material within the main conduit is urged towards the loading structure.

25. A method according to claim 19, wherein, for each process array of the plurality of process arrays, closing the deformable seal comprises deforming a deformable portion of the second side of the body.

26. A method according to claim 19, wherein, for each process array of the plurality of process arrays, closing the deformable seal comprises deforming a deformable metallic layer.

27. A method according to claim 19, wherein, for each process array of the plurality of process arrays, at least a portion of the deformable seal comprises adhesive, and wherein closing the deformable seal comprises adhering the first side and the second side together using the adhesive.

28. A method according to claim 19, wherein, for each process array of the plurality of process arrays, the deformable seal comprises pressure sensitive adhesive located along substantially all of the length of the main conduit, and wherein closing the deformable seal comprises occluding the main conduit along substantially all of its length by adhering the first side and the second side together within the main conduit using the adhesive.

29. A method according to claim 19, wherein, for each process array of the plurality of process arrays, the deformable seal comprises pressure sensitive adhesive located along substantially all of the length of the main conduit, and wherein closing the deformable seal comprises occluding the main conduit along substantially all of its length by adhering the first side and the second side together within the main conduit using the pressure sensitive adhesive, wherein the occluding begins at a point distal from the loading structure and proceeds towards the loading structure, whereby sample material within the main conduit is urged towards the loading structure.

30. A method according to claim 19, wherein, for each process array of the plurality of process arrays, each process chamber of the plurality of process chambers contains at least one reagent before the sample material is distributed.

31. A method of processing sample materials, the method comprising:
   providing a sample processing assembly comprising:
      a sample processing device comprising:
         a body that comprises a first side attached to a second side;
         a plurality of process arrays formed between the first and second sides, wherein each process array of the plurality of process arrays comprises a loading structure, a main conduit comprising a length, and a plurality of process chambers distributed along the main conduit, wherein the main conduit is in fluid communication with the loading structure and the plurality of process chambers;

a carrier attached to the sample processing device, the carrier comprising:
a first surface facing the sample processing device and a second surface facing away from the sample processing device;
a plurality of openings formed through the first and second surfaces of the carrier, wherein each opening of the plurality of openings is aligned with one process chamber of the plurality of process chambers;
distributing sample material to at least some of the process chambers in each process array of the plurality of process arrays through the main conduit in each of the process arrays;
locating the second side of the sample processing device in contact with a thermal block;
selectively compressing the first side and second side of the sample processing device together proximate each process chamber of the plurality of process chambers, the selective compression occurring between the carrier and the thermal block; and
controlling the temperature of the thermal block while the sample processing device is in contact with the thermal block.

32. A method according to claim 31, wherein the selectively compressing comprises compressing substantially all of the sample processing device outside of the process chambers.

33. A method according to claim 31, wherein the carrier comprises compressible material, and further wherein the selectively compressing comprises compressing substantially all of the sample processing device outside of the process chambers.

34. A method according to claim 31, wherein the selectively compressing comprises compressing a discrete area proximate each of the process chambers.

35. A method according to claim 31, wherein the carrier further comprises a plurality of compression structures proximate the first surface of the carrier, each compression structure of the plurality of compression structures proximate one process chamber of the plurality of process chambers, and further wherein the selectively compressing comprises compressing a discrete area proximate each of the process chambers using the compression structures.

36. A method according to claim 31, wherein the carrier further comprises:
a plurality of compression structures proximate the first surface of the carrier, each compression structure of the plurality of compression structures proximate one process chamber of the plurality of process chambers; and
a plurality of force transmission structures, each force transmission structure of the plurality of force transmission structures comprising a discrete landing area proximate the second surface of the carrier, and each force transmission structure of the plurality of force transmission structures being operatively connected to a plurality of the plurality of compression structures;
wherein the selectively compressing comprises applying a force to the landing surface of each force transmission structure, and wherein the force is transmitted to the plurality of compression structures operatively connected to the force transmission structures.

37. A method according to claim 31, wherein the carrier further comprises a plurality of collars proximate the first surface of the carrier, each collar of the plurality of collars aligned with one process chamber of the plurality of process chambers;
and further wherein the selectively compressing comprises compressing a discrete area proximate each of the process chambers with one collar of the plurality of collars.

38. A method according to claim 31, wherein the sample processing device comprises adhesive located between the first side and the second side of the sample processing device, and further wherein the selectively compressing comprises compressing at least a portion of the adhesive.

39. A method according to claim 31, wherein the sample processing device comprises pressure sensitive adhesive located between the first side and the second side of the sample processing device, and further wherein the selectively compressing comprises compressing at least a portion of the pressure sensitive adhesive.

40. A method according to claim 31, wherein, for each process array of the plurality of process arrays, each process chamber of the plurality of process chambers contains at least one reagent before the sample material is distributed.

41. A sample processing assembly comprising:
a sample processing device comprising:
a body that comprises a first side attached to a second side;
a plurality of process arrays formed between the first and second sides, wherein each process array of the plurality of process arrays comprises a loading structure, a main conduit comprising a length, and a plurality of process chambers distributed along the main conduit, wherein the main conduit is in fluid communication with the loading structure and the plurality of process chambers;
a carrier attached to the sample processing device, the carrier comprising:
a first surface facing the sample processing device and a second surface facing away from the sample processing device;
a plurality of openings formed through the first and second surfaces of the carrier, wherein each opening of the plurality of openings is aligned with one process chamber of the plurality of process chambers; and
a plurality of compression structures proximate the first surface of the carrier, each compression structure of the plurality of compression structures proximate one process chamber of the plurality of process chambers.

42. An assembly according to claim 41, wherein each of the compression structures comprises a collar aligned with one of the process chambers.

43. An assembly according to claim 41, further comprising at least one reagent in at least one of the process chambers.

44. An assembly according to claim 41, wherein each process chamber of the plurality of process chambers comprises a volume of about 5 microliters or less.

45. An assembly according to claim 41, wherein the second side of the sample processing device comprises a metallic layer.

46. An assembly according to claim 41, wherein the sample processing device comprises adhesive located between the first side and the second side of the sample processing device.

47. An assembly according to claim 41, wherein the sample processing device comprises pressure sensitive adhesive located between the first side and the second side of the sample processing device.

48. A sample processing assembly comprising:
a sample processing device comprising:
a body that comprises a first side attached to a second side;
a plurality of process arrays formed between the first and second sides, wherein each process array of the plurality of process arrays comprises a loading structure, a main conduit comprising a length, and a plurality of process chambers distributed along the main conduit, wherein the main conduit is in fluid communication with the loading structure and the plurality of process chambers;
a deformable seal located between the loading structure and the plurality of process chambers in each process array of the plurality of process arrays; and
a carrier attached to the sample processing device, the carrier comprising:
a first surface facing the sample processing device and a second surface facing away from the sample processing device;
a plurality of main conduit support rails proximate the first surface of the carrier, wherein each main conduit of the plurality of process arrays is aligned with one main conduit support rail of the plurality of main conduit support rails;
a plurality of openings formed through the first and second surfaces of the carrier, wherein each opening of the plurality of openings is aligned with one process chamber of the plurality of process chambers; and
a plurality of compression structures proximate the first surface of the carrier, each compression structure of the plurality of compression structures proximate one process chamber of the plurality of process chambers.

49. An assembly according to claim 48, wherein each of the compression structures comprises a collar aligned with one of the process chambers.

50. An assembly according to claim 48, further comprising at least one reagent in at least one of the process chambers.

51. An assembly according to claim 48, wherein each process chamber of the plurality of process chambers comprises a volume of about 5 microliters or less.

52. An assembly according to claim 48, wherein the second side of the sample processing device comprises a metallic layer.

53. An assembly according to claim 48, wherein the sample processing device comprises adhesive located between the first side and the second side of the sample processing device.

54. An assembly according to claim 48, wherein the sample processing device comprises pressure sensitive adhesive located between the first side and the second side of the sample processing device.

55. An assembly according to claim 48, wherein, for each process array of the plurality of process arrays, the deformable seal comprises a deformable portion of the second side of the sample processing device.

56. An assembly according to claim 48, wherein, for each process array of the plurality of process arrays, the deformable seal comprises a deformable metallic layer.

57. An assembly according to claim 48, wherein, for each process array of the plurality of process arrays, the deformable seal comprises a deformable portion of the second side of the body, the deformable portion extending along substantially all of the length of the main conduit.

58. An assembly according to claim 48, wherein, for each process array of the plurality of process arrays, the deformable seal comprises adhesive located between the first side and the second side, the adhesive extending along a portion of the length of the main conduit.

59. An assembly according to claim 48, wherein, for each process array of the plurality of process arrays, the deformable seal comprises adhesive located between the first side and the second side, the adhesive extending along substantially all of the length of the main conduit.

60. An assembly according to claim 48, wherein, for each process array of the plurality of process arrays, the deformable seal comprises conformable seal material.

61. An assembly according to claim 48, wherein, for each process array of the plurality of process arrays, the deformable seal comprises expandable seal material.

62. A method of processing sample materials, the method comprising:
providing a sample processing assembly comprising:
a sample processing device comprising:
a body that comprises a first side attached to a second side;
a plurality of process arrays formed between the first and second sides, wherein each process array of the plurality of process arrays comprises a loading structure, a main conduit comprising a length, and a plurality of process chambers distributed along the main conduit, wherein the main conduit is in fluid communication with the loading structure and the plurality of process chambers;
a deformable seal located between the loading structure and the plurality of process chambers in each process array of the plurality of process arrays; and
a carrier attached to the sample processing device, the carrier comprising:
a first surface facing the sample processing device and a second surface facing away from the sample processing device;
a plurality of main conduit support rails proximate the first surface of the carrier, wherein each main conduit of the plurality of process arrays is aligned with one main conduit support rail of the plurality of main conduit support rails; and
a plurality of openings formed through the first and second surfaces of the carrier, wherein each opening of the plurality of openings is aligned with one process chamber of the plurality of process chambers;
distributing sample material to at least some of the process chambers in each process array of the plurality of process arrays through the main conduit in each of the process arrays;
closing the deformable seal in each process array of the plurality of process arrays, the closing comprising supporting the main conduit with one of the main conduit support rails while compressing the first side and the second side of the sample processing device together along at least a portion of the length of the main conduit;
locating the second side of the sample processing device in contact with a thermal block;
selectively compressing the first side and second side of the sample processing device together proximate each process chamber of the plurality of process chambers, the selective compression occurring between the carrier and the thermal block; and controlling the temperature of the thermal block while the sample processing device is in contact with the thermal block.

63. A method according to claim 62, wherein closing the deformable seal in each process array of the plurality of process arrays comprises simultaneously closing the deformable seal in each process array of the plurality of process arrays.

64. A method according to claim 62, wherein, for each process array of the plurality of process arrays, closing the deformable seal comprises occluding the main conduit along substantially all of its length.

65. A method according to claim 62, wherein, for each process array of the plurality of process arrays, closing the deformable seal comprises occluding the main conduit along only a portion of its length.

66. A method according to claim 62, wherein, for each process array of the plurality of process arrays, closing the deformable seal comprises occluding the main conduit along substantially all of its length beginning at a point distal from the loading structure and proceeding towards the loading structure, whereby sample material within the main conduit is urged towards the loading structure.

67. A method according to claim 62, wherein, for each process array of the plurality of process arrays, closing the deformable seal comprises occluding only a portion of the length of the main conduit beginning at a point distal from the loading structure and proceeding towards the loading structure, whereby sample material within the main conduit is urged towards the loading structure.

68. A method according to claim 62, wherein, for each process array of the plurality of process arrays, closing the deformable seal comprises deforming a deformable portion of the second side of the body.

69. A method according to claim 62, wherein, for each process array of the plurality of process arrays, closing the deformable seal comprises deforming a deformable metallic layer.

70. A method according to claim 62, wherein, for each process array of the plurality of process arrays, at least a portion of the deformable seal comprises adhesive, and wherein closing the deformable seal comprises adhering the first side and the second side together using the adhesive.

71. A method according to claim 62, wherein, for each process array of the plurality of process arrays, the deformable seal comprises pressure sensitive adhesive located along substantially all of the length of the main conduit, and wherein closing the deformable seal comprises occluding the main conduit along substantially all of its length by adhering the first side and the second side together within the main conduit using the adhesive.

72. A method according to claim 62, wherein, for each process array of the plurality of process arrays, the deformable seal comprises pressure sensitive adhesive located along substantially all of the length of the main conduit, and wherein closing the deformable seal comprises occluding the main conduit along substantially all of its length by adhering the first side and the second side together within the main conduit using the adhesive, wherein the occluding begins at a point distal from the loading structure and proceeds towards the loading structure, whereby sample material within the main conduit is urged towards the loading structure.

73. A method according to claim 62, wherein, for each process array of the plurality of process arrays, each process chamber of the plurality of process chambers contains at least one reagent before the sample material is distributed.

74. A method according to claim 62, wherein the selectively compressing comprises compressing substantially all of the sample processing device outside of the process chambers.

75. A method according to claim 62, wherein the carrier comprises compressible material, and further wherein the selectively compressing comprises compressing substantially all of the sample processing device outside of the process chambers.

76. A method according to claim 62, wherein the selectively compressing comprises compressing a discrete area proximate each of the process chambers.

77. A method according to claim 62, wherein the carrier further comprises a plurality of collars proximate the first surface of the carrier, each collar of the plurality of collars aligned with one process chamber of the plurality of process chambers; and further wherein the selectively compressing comprises compressing a discrete area proximate each of the process chambers with one collar of the plurality of collars.

78. A method according to claim 62, wherein the sample processing device comprises adhesive located between the first side and the second side of the sample processing device, and further wherein the selectively compressing comprises compressing at least a portion of the adhesive.

79. A method according to claim 62, wherein the sample processing device comprises pressure sensitive adhesive located between the first side and the second side of the sample processing device, and further wherein the selectively compressing comprises compressing at least a portion of the pressure sensitive adhesive.

80. A method of processing sample materials, the method comprising:
providing a sample processing assembly comprising:
a sample processing device comprising:
a body that comprises a first side attached to a second side;
a plurality of process arrays formed between the first and second sides, wherein each process array of the plurality of process arrays comprises a loading structure, a main conduit comprising a length, and a plurality of process chambers distributed along the main conduit, wherein the main conduit is in fluid communication with the loading structure and the plurality of process chambers;
a deformable seal located between the loading structure and the plurality of process chambers in each process array of the plurality of process arrays; and
a carrier attached to the sample processing device, the carrier comprising:
a first surface facing the sample processing device and a second surface facing away from the sample processing device;
a plurality of main conduit support rails proximate the first surface of the carrier, wherein each main conduit of the plurality of process arrays is aligned with one main conduit support rail of the plurality of main conduit support rails; and
a plurality of openings formed through the first and second surfaces of the carrier, wherein each opening of the plurality of openings is aligned with one process chamber of the plurality of process chambers;
distributing sample material to at least some of the process chambers in each process array of the plurality of process arrays through the main conduit in each of the process arrays;

closing the deformable seal in each process array of the plurality of process arrays, the closing comprising supporting the main conduit with one of the main conduit support rails while compressing the first side and the second side of the sample processing device together along at least a portion of a length of the main conduit;

separating the loading structure of each process array of the plurality of process arrays from the sample processing device;

locating the second side of the sample processing device in contact with a thermal block; and controlling the temperature of the thermal block while the sample processing device is in contact with the thermal block.

81. A method according to claim 80, wherein the loading structures comprise loading chambers, and wherein the method further comprises sealing the loading chambers before separating the loading structures from the sample processing device.

82. A method according to claim 80, wherein, for each process array of the plurality of process arrays, the loading structure comprises a loading chamber comprising an inlet port and a vent port, and wherein the method further comprises sealing the inlet port and the vent port before separating the loading structures from the sample processing device.

83. A method of processing sample materials, the method comprising:
   providing a sample processing assembly comprising:
      a sample processing device comprising:
         a body that comprises a first side attached to a second side;
         a plurality of process arrays formed between the first and second sides, wherein each process array of the plurality of process arrays comprises a loading chamber, a main conduit comprising a length, and a plurality of process chambers distributed along the main conduit, wherein the main conduit is in fluid communication with the loading chamber and the plurality of process chambers;
         a deformable seal located between the loading chamber and the plurality of process chambers in each process array of the plurality of process arrays; and
      a carrier attached to the sample processing device, the carrier comprising:
         a first surface facing the sample processing device and a second surface facing away from the sample processing device;
         a plurality of main conduit support rails proximate the first surface of the carrier, wherein each main conduit of the plurality of process arrays is aligned with one main conduit support rail of the plurality of main conduit support rails; and
         a plurality of openings formed through the first and second surfaces of the carrier, wherein each opening of the plurality of openings is aligned with one process chamber of the plurality of process chambers;

distributing sample material to at least some of the process chambers in each process array of the plurality of process arrays through the main conduit in each of the process arrays;

closing the deformable seal in each process array of the plurality of process arrays, the closing comprising supporting the main conduit with one of the main conduit support rails while compressing the first side and the second side of the sample processing device together along at least a portion of the length of the main conduit;

separating the loading chambers of each process array of the plurality of process arrays from the sample processing device;

selectively compressing the first side and second side of the sample processing device together proximate each process chamber of the plurality of process chambers, the selective compression occurring between the carrier and the thermal block;

locating the second side of the sample processing device in contact with a thermal block; and controlling the temperature of the thermal block while the sample processing device is in contact with the thermal block.

84. A method according to claim 83, wherein the selectively compressing comprises compressing substantially all of the sample processing device outside of the process chambers.

85. A method according to claim 83, wherein the selectively compressing comprises compressing a discrete area proximate each of the process chambers.

86. A method according to claim 83, wherein, for each process array of the plurality of process arrays, closing the deformable seal comprises occluding the main conduit beginning at a point distal from the loading chamber and proceeding towards the loading chamber, whereby sample material within the main conduit is urged towards the loading chamber.

* * * * *